(12) United States Patent
Donde et al.

(10) Patent No.: US 7,183,324 B2
(45) Date of Patent: Feb. 27, 2007

(54) 2,3,4-SUBSTITUTED CYCLOPENTANONES AS THERAPEUTIC AGENTS

(75) Inventors: Yariv Donde, Dana Point, CA (US); Mark Holoboski, Laguna Niguel, CA (US); Mari F. Posner, Laguna Niguel, CA (US); Robert M. Burk, Laguna Beach, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 267 days.

(21) Appl. No.: 10/997,039

(22) Filed: Nov. 23, 2004

(65) Prior Publication Data

US 2006/0111430 A1    May 25, 2006

(51) Int. Cl.
*A61K 31/095* (2006.01)
*A61K 31/38* (2006.01)
*C07C 331/00* (2006.01)
*C07D 333/56* (2006.01)

(52) U.S. Cl. .......................... 514/706; 568/75; 568/77; 549/58; 514/443

(58) Field of Classification Search ................ 514/706, 514/443; 568/75, 76; 549/58
See application file for complete search history.

(56) References Cited

U.S. PATENT DOCUMENTS

| | | | |
|---|---|---|---|
| 4,131,738 A | 12/1978 | Smith | 560/546 |
| 4,147,877 A | 4/1979 | Smith | 560/562 |
| 4,166,452 A | 9/1979 | Generales, Jr. | 128/741 |
| 4,256,108 A | 3/1981 | Theeuwes | 128/260 |
| 4,265,874 A | 5/1981 | Bonsen et al. | 424/415 |
| 6,043,275 A | 3/2000 | Maruyama et al. | 514/530 |
| 6,410,591 B1 | 6/2002 | Burk et al. | |
| 6,538,018 B1 | 3/2003 | Burk et al. | |
| 6,552,067 B2 | 4/2003 | Cameron et al. | 514/424 |
| 6,586,468 B1 | 7/2003 | Maruyama et al. | 514/530 |
| 7,101,906 B2 * | 9/2006 | Donde et al. | 514/443 |

FOREIGN PATENT DOCUMENTS

| | | |
|---|---|---|
| GB | 1601994 | 11/1981 |
| WO | WO 02/102389 | 12/2002 |

OTHER PUBLICATIONS

Carey, Francis A., Organic Chemistry, New York: McGraw-Hill Book Company 1987, p. 63.
Chourasia, M.K., and Jain, S.K. *Pharmaceutical approaches to colon targeted drug delivery systems*, J Pharm Pharmaceut Sci 6 (1): 33-66, 2003.
Kabashima, K. et. al., *The prostaglandin receptor EP4 suppresses colitis, mucosal damage and CD4 cell activation in the gut*, The Journal of Clinical Investigation, Apr. 2002, vol. 9, 883-893.
Remington's Pharmaceutical Sciences, Mack Publishing Company, Easton, Pa., 16th Edition, 1980.
Shareef, M.A., et. al *Colonic Drug Delivery: an Updated Review*, AAPS PharmSci 2003; 5 (2) Article 17.

\* cited by examiner

*Primary Examiner*—Deborah C. Lambkin
(74) *Attorney, Agent, or Firm*—Brent A. Johnson; Robert J. Baran; Martin A. Voet

(57) ABSTRACT

Disclosed herein are compounds comprising

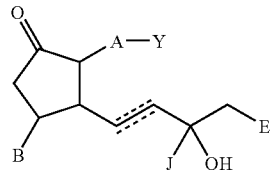

or a pharmaceutically acceptable salt or a prodrug thereof; wherein Y, A, B, J, and E are further described.

Figure 1:
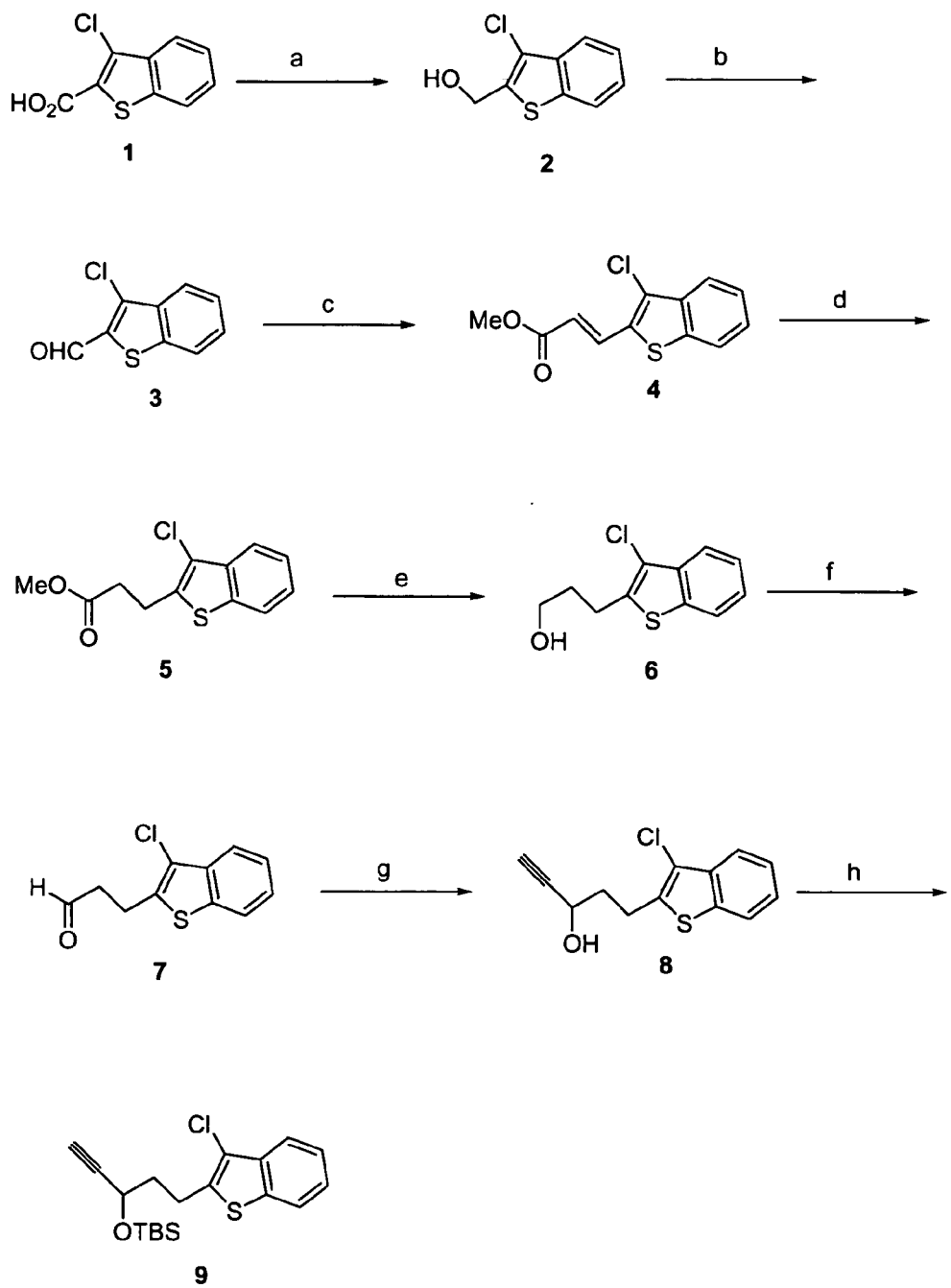

Methods, compositions, and medicaments related thereto are also disclosed.

28 Claims, 7 Drawing Sheets

(a) LiAlH$_4$; (b) TPAP, NMO; (c) Ph$_3$P=CHCO$_2$Me; (d) (Ph$_3$P)$_3$RhCl, H$_2$; (e) LiBH$_4$;
(f) Swern [O]; (g) ethynylmagnesium bromide; (h) TBSCl, DMAP, Et$_3$N.

(a) Cp$_2$ZrHCl, THF; (b) MeLi, Et$_2$O -78 °C; (c) 2-thienylCuCNLi, THF -78 °C; (d) enone, THF -78 °C; (e) TBSOTf, Et$_3$N, CH$_2$Cl$_2$; (f) Amberlyst 15; (g) MeLi, CuCN; (h) HF-pyridine, CH$_3$CN.

Rf high (141a) / Rf low (141b)

Rf high (140a)
Rf low (140b)

2,3,4-SUBSTITUTED CYCLOPENTANONES AS THERAPEUTIC AGENTS

FIELD OF THE INVENTION

This invention relates to therapeutically active agents. Particularly this invention relates to compounds which are prostaglandin or prostamide receptor agonists.

BACKGROUND OF THE INVENTION

Description of Related Art

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

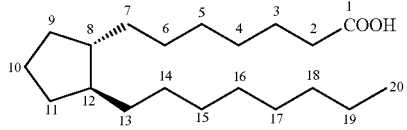

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

U.S. Pat. Nos. 4,131,738 and 4,147,877 disclose certain 6-hydroxy, 11-dihydro and 11 hydroxymethyl prostaglandin E derivatives.

British patent 1601994 discloses certain 11-dihydro and 11-alkyl prostaglandin E derivatives.

Prostaglandin $EP_4$ selective agonists are believed to have several medical uses. For example, U.S. Pat. No. 6,552,067 B2 teaches the use of prostaglandin EP4 selective agonists for the treatment of "methods of treating conditions which present with low bone mass, particularly osteoporosis, frailty, an osteoporotic fracture, a bone defect, childhood idiopathic bone loss, alveolar bone loss, mandibular bone loss, bone fracture, osteotomy, bone loss associated with periodontitis, or prosthetic ingrowth in a mammal".

U.S. Pat. No. 6,586,468 B1 teaches that prostaglandin EP4 selective agonists "are useful for the prophylaxis and/or treatment of immune diseases (autoimmune diseases (amyotrophic lateral sclerosis (ALS), multiple sclerosis, Sjoegren's syndrome, arthritis, rheumatoid arthritis, systemic lupus erythematosus, etc.), post-transplantation graft rejection, etc.), asthma, abnormal bone formation, neurocyte death, pulmopathy, hepatopathy, acute hepatitis, nephritis, renal insufficiency, hypertension, myocardial ischemia, systemic inflammatory syndrome, pain induced by ambustion, sepsis, hemophagocytosis syndrome, macrophage activation syndrome, Still's diseases, Kawasaki diseases, burn, systemic granuloma, ulcerative colitis, Crohn's diseases, hypercytokinemia at dialysis, multiple organ failure, shock, etc. They are also connected with sleeping disorders and platelet coagulations, and therefore they are thought to be useful for these diseases."

Inflammatory bowel disease (IBD) is a group of disease characterized by inflammation in the large or small intestines and is manifest in symptoms such as diarrhea, pain, and weight loss. Nonsteroidal anti-inflammatory drugs have been shown to be associated with the risk of developing IBD, and recently Kabashima and colleagues have disclosed that "EP4 works to keep mucosal integrity, to suppress the innate immunity, and to downregulate the proliferation and activation of CD4+ T cells. These findings have not only elucidated the mechanisms of IBD by NSAIDs, but also indicated the therapeutic potential of EP4-selective agonists in prevention and treatment of IBD." (Kabashima, et. al., The Journal of Clinical Investigation, April 2002, Vol. 9, 883–893)

BRIEF DESCRIPTION OF THE INVENTION

Disclosed herein are compounds comprising

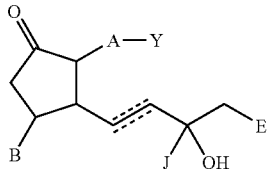

or a pharmaceutically acceptable salt or a prodrug thereof;

wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_qG(CH_2)_r G(CH_2)_s-$, wherein G is S or O, r is at least 2, and wherein $q+r+s=4$;

B is hydrogen, CN, $CO_2H$, $C_{1-6}$ hydrocarbyl, or $-(CH_2)_m X(CH_2)_p H$, wherein m is at least 1 and the sum of m and p is from 1 to 5;

X is S or O;

J is H, $CH_3$, or $CF_3$; and

E is a moiety comprising a covalently bonded chain of from 2 to 13 atoms.

Methods, compositions, and medicaments related thereto are also disclosed.

BRIEF DESCRIPTION OF THE DRAWING FIGURES

Figure 2:
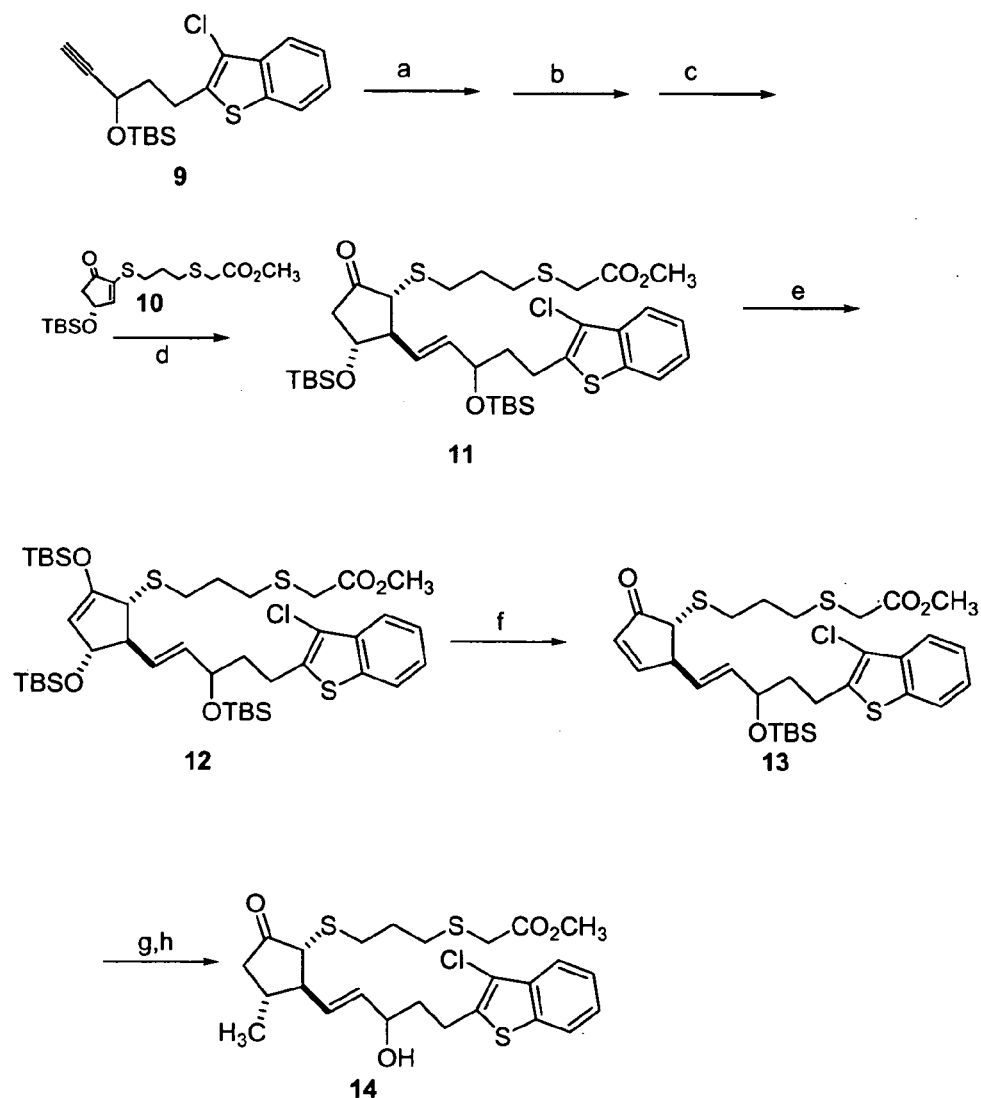
Figure 3:
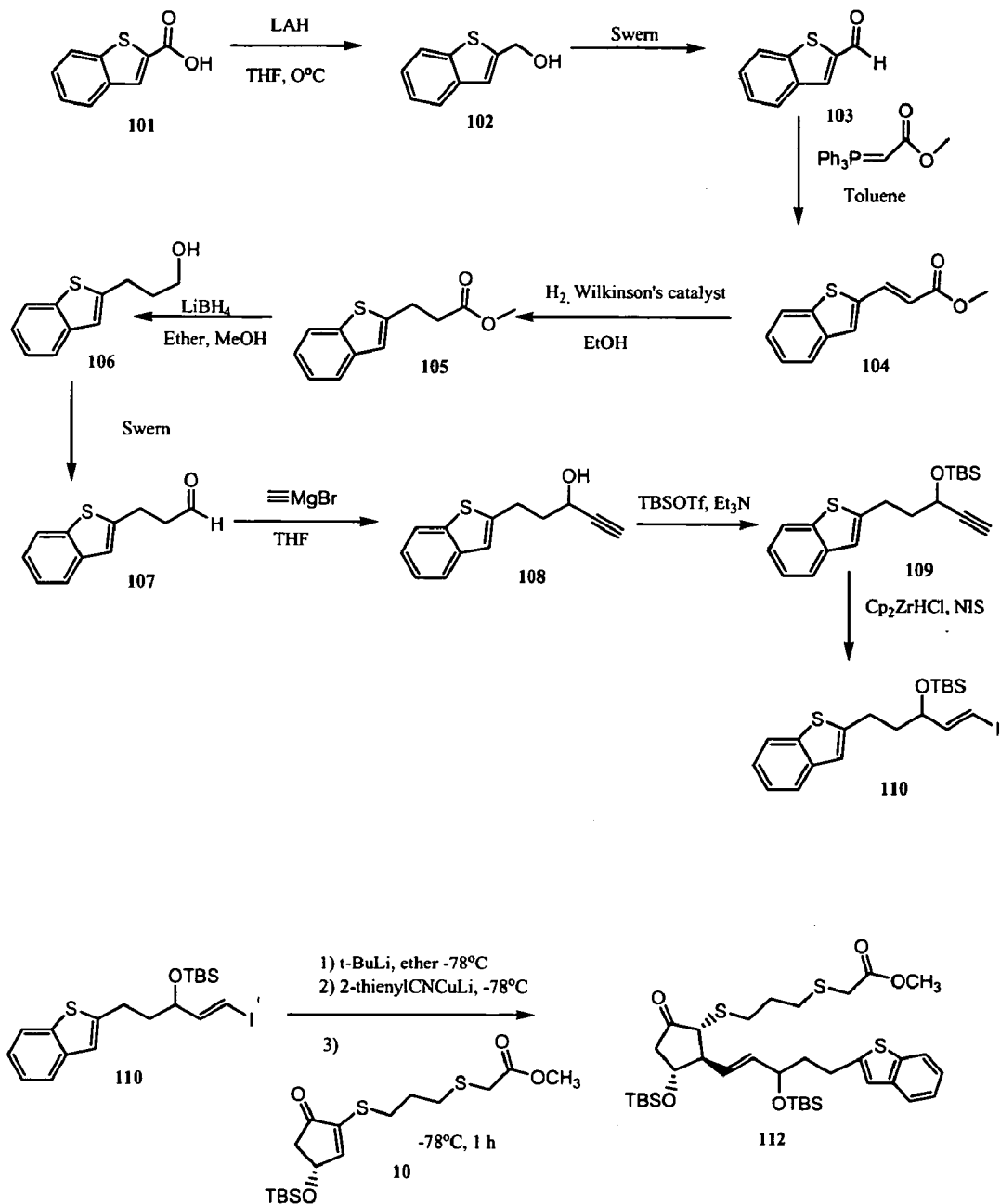
Figure 4:
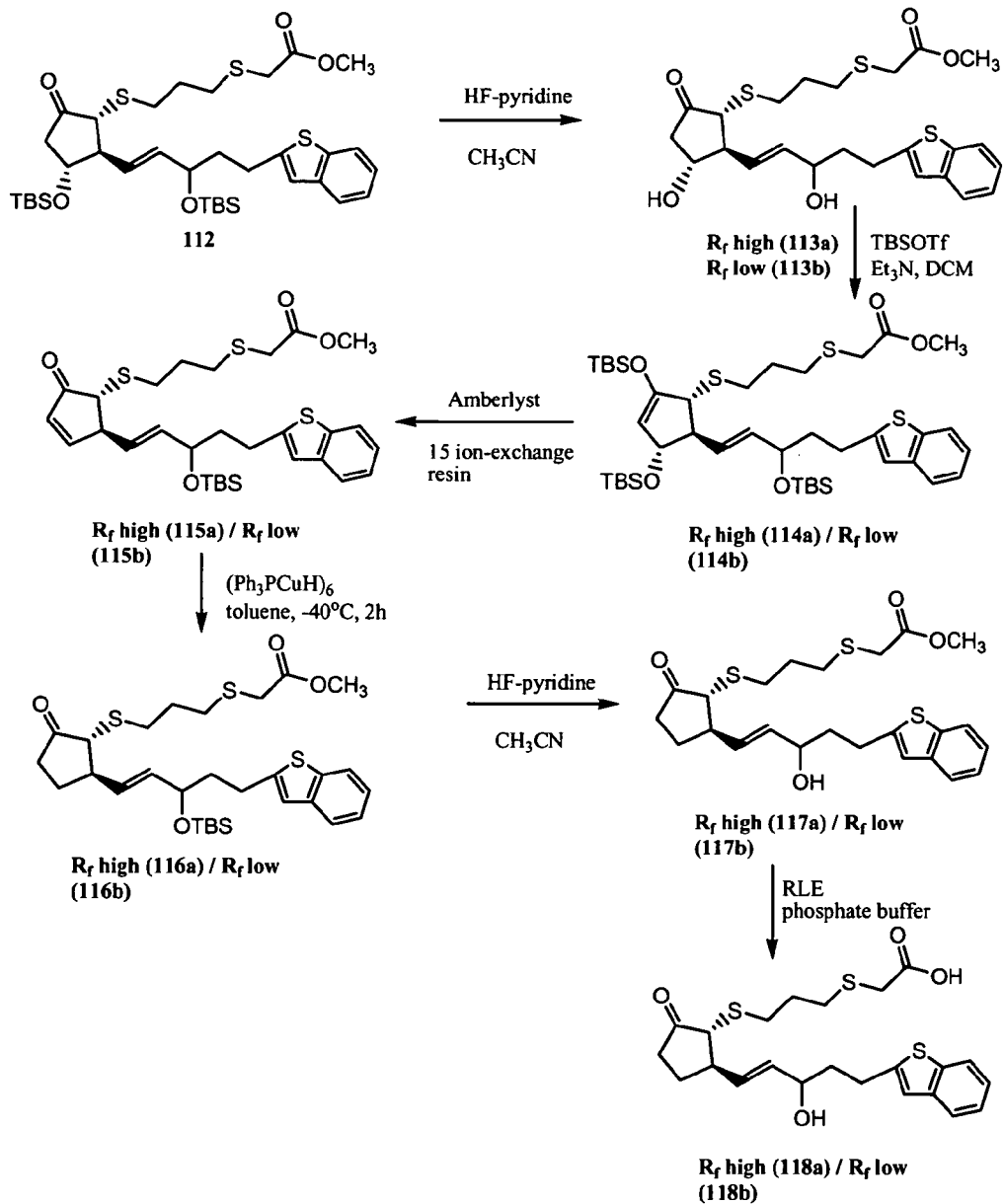
Figure 5:
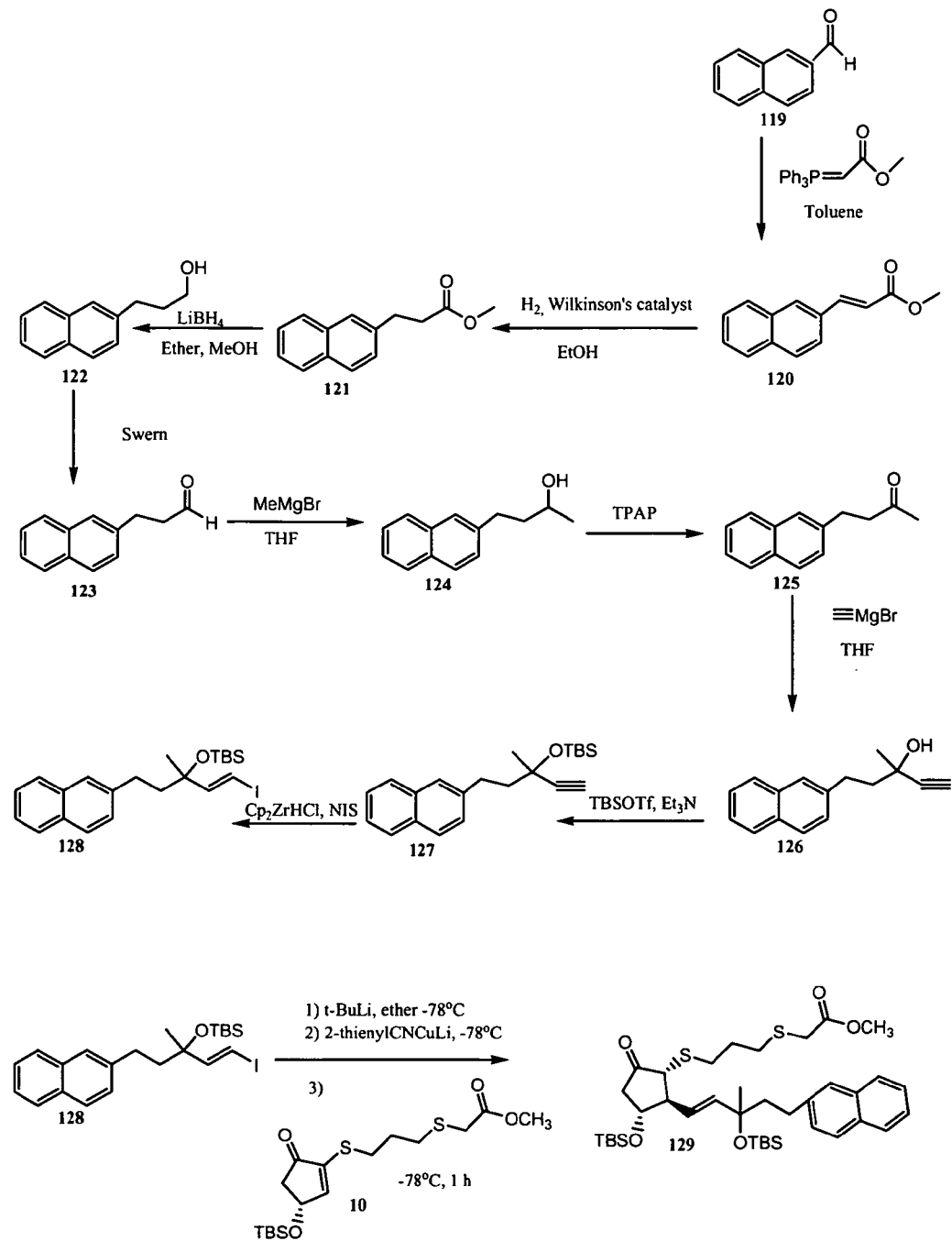
Figure 6:
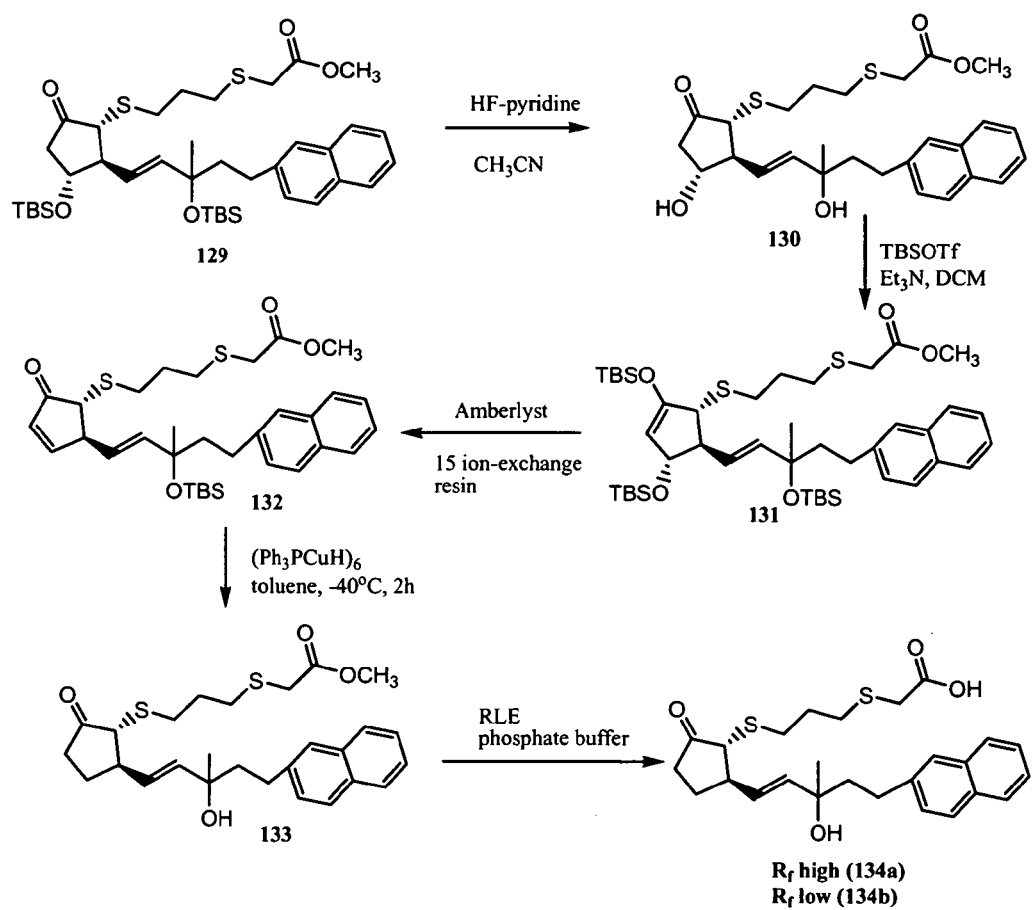
Figure 7:
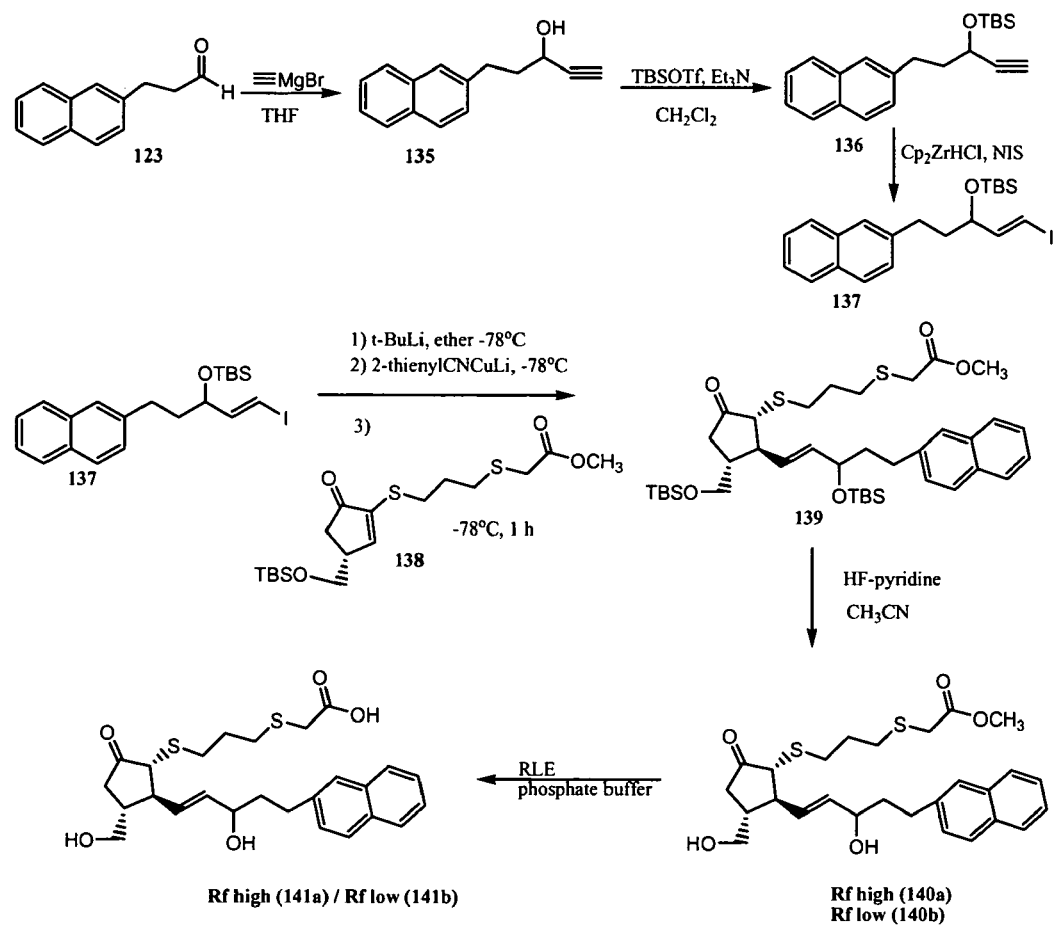

FIGS. 1–7 demonstrate some methods of preparing the compounds disclosed herein.

DETAILED DESCRIPTION OF THE INVENTION

In the structural representations of the compounds disclosed herein, dashed line represents the presence or absence of a bond.

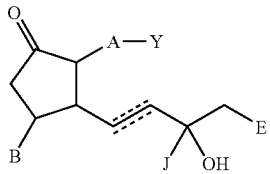

In other words, the structure shown above represents any compound which may be described by one of the structures shown below.

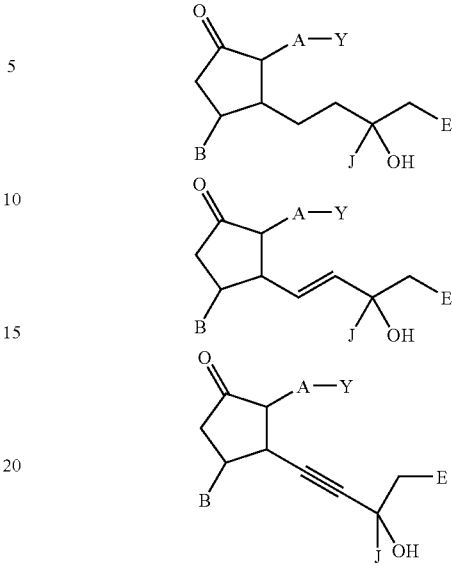

While not intending to limit the scope of the invention in any way, compounds having the stereochemistry shown in the structural formula below are particularly useful.

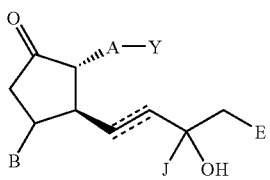

In addition, compounds having the indicated stereochemistry at one of the bonds in the structure above are also useful, i.e. compounds having the structures indicated below.

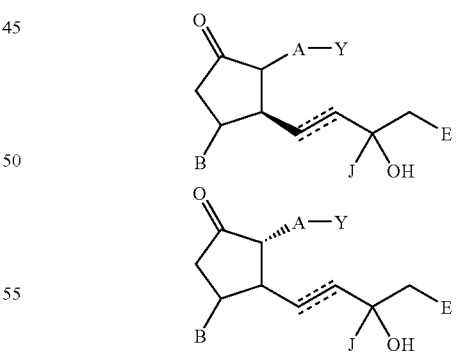

As with any structure disclosed herein, pharmaceutically acceptable salts or prodrugs of compounds represent by the above structures are also contemplated.

A person of ordinary skill in the art understands the meaning of the stereochemistry associated with the hatched wedge/solid wedge structural features. For example, an introductory organic chemistry textbook (Francis A. Carey, Organic Chemistry, New York: McGraw-Hill Book Company 1987, p. 63) states "a wedge indicates a bond coming from the plane of the paper toward the viewer" and the hatched wedge, indicated as a "dashed line," "represents a bond receding from the viewer."

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group. Thus, while not intending to limit the scope of the invention in any way, in certain compounds Y is a carboxylic acid, sulfonic acid, or phosphonic acid functional group, i.e. one of the structures shown below.

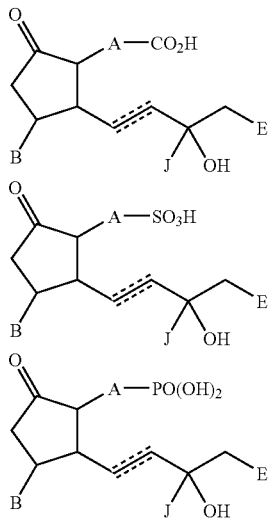

Salts of any of these acids of any pharmaceutically acceptable form may also be present.

Additionally, an amide or ester of one of the organic acids shown above comprising from 0 to 12 carbon atoms is also contemplated. In an ester, a hydrocarbyl moiety replaces a hydrogen atom of an acid such as in a carboxylic acid ester, e.g. $CO_2R^2$. In an amide, an amine group replaces an OH of the acid. An amine is a moiety with a central nitrogen that has exactly three bonds to C or H. Examples of amides include $CON(R^2)_2$, $CON(OR^2)R^2$, $CON(CH_2CH_2OH)_2$, and $CONH(CH_2CH_2OH)$. Moieties such as $CONHSO_2R^2$ are also amides of the carboxylic acid notwithstanding the fact that they may also be considered to be amides of the sulfonic acid $R^2$—$SO_3H$.

While not intending to limit the scope of the invention in any way, Y may also be hydroxymethyl or an ether thereof comprising from 0 to 12 carbon atoms. Thus, compounds having a structure shown below are possible.

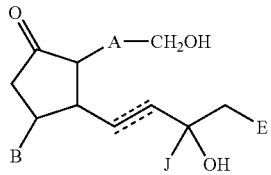

Additionally, ethers of these compounds are also possible. An ether is defined as a functional group wherein a hydrogen of an hydroxyl is replaced by carbon, e.g., Y is $CH_2OCH_3$, $CH_2OCH_2CH_3$, etc.

Finally, while not intending to limit the scope of the invention in any way, Y may be a tetrazolyl functional group, i.e. compounds having a structure such as one of those shown below.

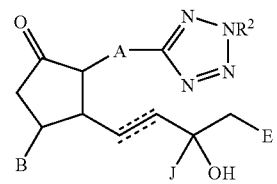

When $R^2$ is hydrogen, the tetrazolyl functional group has two tautomeric forms, which can rapidly interconvert in aqueous or biological media, and are thus equivalent to one another. These tautomers are shown below.

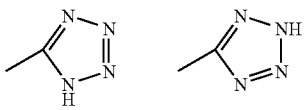

Additionally, if $R^2$ is $C_1$–$C_6$ alkyl, phenyl, or biphenyl, other isomeric forms of the tetrazolyl functional group such as the one shown below are also possible, all of these are considered to be within the scope of the term "tetrazolyl".

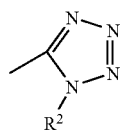

While not intending to limit the scope of the invention in any way, in one embodiment, Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and tetrazolyl-$R^2$; wherein $R^2$ is independently H, $C_1$–$C_6$ alkyl, phenyl, or biphenyl.

A is —$(CH_2)_qG(CH_2)_rG(CH_2)_s$—, wherein G is S or O, r is at least 2, and wherein q+r+s=4. Thus, while not intending to be limiting, in one embodiment, G is S such that A is one of the groups shown below, or the like.

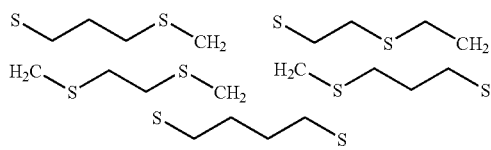

In another embodiment, G is O such that A is one of the groups shown below, or the like.

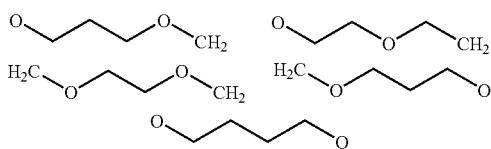

In another embodiment, G is both O and S such that A is one of the groups shown below, or the like.

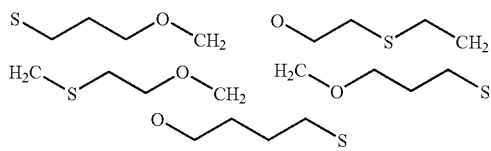

B is hydrogen, CN, CO$_2$H, C$_{1-6}$ hydrocarbyl, or —(CH$_2$)$_m$X(CH$_2$)$_p$H, wherein m is at least 1 and the sum of m and p is from 1 to 5. Thus, compounds according to the structures below are contemplated, as well as pharmaceutically acceptable salts or prodrugs thereof.

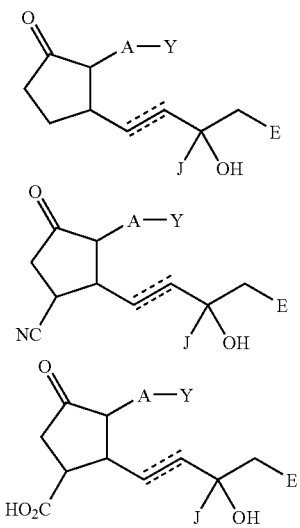

Alternatively, B is C$_{1-6}$ hydrocarbyl. Hydrocarbyl is a moiety having only carbon and hydrogen such as a C$_{1-6}$ alkyl including methyl, ethyl, and the like; C$_{2-6}$ alkenyl such as ethenyl or the like; C$_{2-6}$ alkynyl; phenyl; or the like. Alkyl is hydrocarbyl having no double or triple bonds, which may be linear, such as n-butyl; cyclic, such as cyclobutyl; branched, such as t-butyl; or any combination thereof. Alkenyl should be broadly understood to be hydrocarbyl having one or more C═C bonds but no triple bonds, which may be linear, branched, cyclic, or a combination thereof. While not intending to be limiting, typical examples are ethenyl, propenyl, butadienyl; cyclopentenyl; and the like. Alkynyl should be broadly understood to be hydrocarbyl having one or more C≡C bonds such as ethynyl, propynyl; butadiynyl, and the like. Combinations of any of the above are also possible.

In one embodiment, B is hydrocarbyl having from 1 to 4 carbon atoms. In another embodiment, B is hydrocarbyl having from 1 to 3 carbon atoms. In other embodiments, B is alkyl having from 1 to 3 carbon atoms. In other embodiments, B is alkylene having from 2 to 3 carbon atoms.

Alternatively, B may be —(CH$_2$)$_m$X(CH$_2$)$_p$H, wherein m is at least 1 and the sum of m and p is from 1 to 5, and X is S or O; i.e. there are from 1 to 5 methylene (CH$_2$) groups and an S or an O atom. Thus, B may be an ethereal moiety having from 1 to 5 carbon atoms such as —CH$_2$OCH$_3$, —CH$_2$CH$_2$OCH$_3$, etc.; or a hydroxyalkyl having from one to five carbon atoms such as hydroxymethyl (—CH$_2$OH), hydroxyethyl, etc. Sulfur containing analogs are also possible, i.e. where X is S. In one embodiment, the sum of m and p is from 1 to 3. In another embodiment, B is C$_{1-3}$ hydroxyalkyl.

J is H, CH$_3$, or CF$_3$. In other words, while not intending to limit the scope of the invention in any way, compounds represented by the structural formula below are possible.

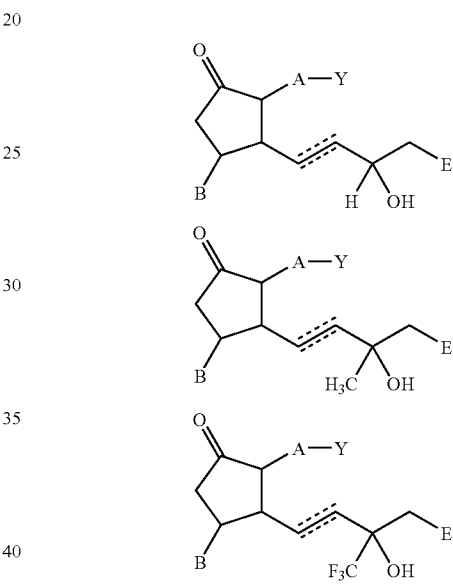

As with any structure disclosed herein, pharmaceutically acceptable salts or prodrugs of compounds represent by the above structures are also contemplated.

E is a moiety comprising a covalently bonded chain of from 2 to 13 atoms. In other words, the most remote atom of E is part of a chain of from 2 to 13 atoms connected to the remainder of molecule. The most remote atom is the atom which is part of the longest covalently bonded chain, determined in the most direct manner, to the remainder of the molecule. A covalently bonded chain is a chain of atoms connected by a series of covalent bonds in a linear fashion. Thus, if E is methyl, it has a covalently bonded chain of 2 atoms, i.e. carbon and hydrogen, as indicated by the numbers below.

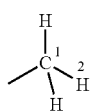

Similarly, an n-hexyl moiety comprises a chain of 7 atoms.

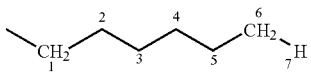

E may comprise atoms which are not part of the chain, provided that the most remote of these atoms does not complete a chain of more than 13 atoms, determined in the most direct manner. The most direct manner is the manner of connecting two atoms which involves the least number of serially bonded atoms.

Thus, the group shown below comprises a chain of 7 atoms as indicated by the numbering below. Since counting around the ring includes 11 atoms, the manner indicated by the numbering below is the most direct route to the most remote atom.

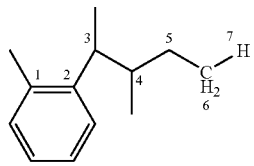

While not intending to be limiting, certain moieties are specifically contemplated for E. In one embodiment, E is a $C_{2-5}$ alkyl moiety. In another embodiment, E is n-butyl.

In another embodiment E is R or $CH_2$—R, wherein R is an aromatic or heteroaromatic moiety having from 0 to 4 substituents. Thus, while not intending to limit the scope of the invention in any way, R may be unsubsituted benzene, or mono-, di-, tri-, or tetrasubstituted phenyl. The substituents may comprise up to 6 non-hydrogen atoms each. In other words, the substituent will have up to 6 atoms which are not hydrogen, including C, N, S, O, P, F, Cl, Br, I, etc., and will have any number of hydrogen atoms required by the circumstances. Thus, while not intending to limit the scope of the invention in any way, the substituents may include hydrocarbyl up to $C_6$ such as alkyl, alkylenyl, alkynyl, and the like, whether linear, branched, cyclic, or a combination thereof; hydrocarbyloxy up to $C_5$ such as methoxy, ethoxy, and the like; acyl up to $C_5$; acyloxy up to $C_4$; $CO_2H$ and salts; $SO_3H$ and salts; $PO(OH)_2$ and salts; sulfonyl up to $C_3$, phosphonyl up to $C_3$; $NO_2$; CN; halogens such as fluoro, chloro, and bromo; fluorocarbyl such as $CF_3$; amines having up to 5 carbon atoms; and the like. A counterion of a salt is not counted as part of a substituent. For example, $CO_2^-Na^+$ is considered to have 3 non-hydrogen atoms since $Na^+$ is not counted. If more than one substituent is present, they may be identical or present in any combination.

Alternatively, R may be an unsubstituted heteroaromatic ring such as pyridyl, pyrimidinyl, pyrazinyl, pyradazinyl, thienyl, furyl, pyrrolyl, thiazolyl, imidazolyl, and the like. Or R may be a mono, di, tri, or tetrasubstituted heteroaromatic ring. Certain rings however, may not be capable of bearing up to 4 substitutents, in which case these rings may have as many substituents as the ring will bear.

Alternatively, R may be a bicyclic aromatic or heteroaromatic system. In other words, R is a bicyclic ring system which has an aromatic ring in it. While not intending to limit the scope of the invention in any way, only one of the two rings need be aromatic, such as in for example, tetrahydrobenzofuryl or tetrahydronapthyl. Alternatively, both rings in the system may be aromatic.

Bicyclic aromatic systems include naphthyl, tetrahydronapthyl, and the like. Bicyclic heteroaromatic ring systems are also contemplated. Examples of such ring systems include, but are not limited to, ring systems with one heteroatom and ring systems with more than one heteroatom. Ring systems with one heteroatom include those having a sulfur atom such as benzothienyl and isobenzothienyl; those having an oxygen atom such as benzofuryl and isobenzofuryl; and those having a nitrogen atom such as quinolinyl, isoquinolinyl, indolyl, isobenzofuryl, isondolyl, benzopyridyl, and the like. Ring systems with more than one heteroatom include moieties such as benzimidazolyl, benzothiazolyl, benzopyrimidyl, benzopyrazinyl, and the like.

While not intending to be limiting, in certain embodiments E is $CH_2$—R, wherein R is a bicyclic aromatic or heteroaromatic ring system which may have up to 2 substituents selected from the group consisting of methyl, ethyl, fluoro, bromo, chloro, trifluoromethyl, methoxy, and $NO_2$. In other embodiments E is phenyl, benzyl, phenoxy, or phenylthio. In other embodiments R is naphthyl or benzothienyl, i.e. E is naphthyl, benzothienyl, $CH_2$-napthyl, or $CH_2$-benzothienyl. In other embodiments E is naphthyl, benzothienyl, $CH_2$-napthyl, or $CH_2$-benzothienyl which may have up to 4 substituents, wherein said substituents comprise up to 6 non-hydrogen atoms. In other embodiments E is naphthyl, benzothienyl, $CH_2$-napthyl, or $CH_2$-benzothienyl which may have up to 2 substituents selected from the group consisting of methyl, ethyl, fluoro, bromo, chloro, trifluoromethyl, methoxy, and $NO_2$.

While not intending to be limiting, in certain compounds E is $R^1$ or $Z-R^1$, wherein $R^1$ is a bicyclic aromatic or heteroaromatic ring system having from 0 to 4 substituents having up to 6 non-hydrogen atoms, and wherein Z is O, S, or $CH_2$. Thus, E may be $R^1$, $CH_2R^1$, $OR^1$, or $SR^1$, or substituted derivatives thereof as described. In certain embodiments $R^1$ is naphtyl, benzothienyl, or substituted napthyl or benzothienyl having from 0 to 4 substituents having up to 6 non-hydrogen atoms, and wherein Z is O, S, or $CH_2$. In other compounds $R^1$ is napthyl, benzothienyl, or substituted napthyl or benzothienyl having up to 2 substituents selected from the group consisting of methyl, ethyl, fluoro, bromo, chloro, trifluoromethyl, methoxy, and $NO_2$.

Other compounds include those characterized by the structure below, or a pharmaceutically acceptable salt or a prodrug thereof.

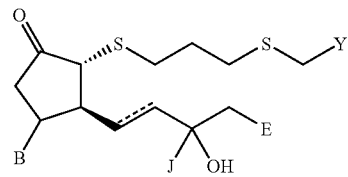

Other compounds include those characterized by the structure below, or a pharmaceutically acceptable salt or a prodrug thereof.

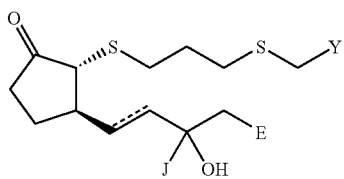

The compound shown below, or a pharmaceutically acceptable salt or a prodrug thereof, is particularly useful.

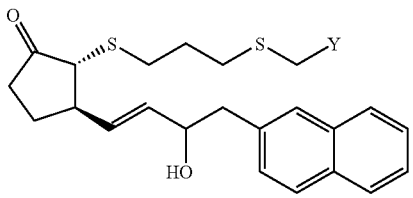

The following compounds are specifically contemplated herein:

{3-[(1R,2R)-2-((E)-3-Hydroxy-3-methyl-5-naphthalen-2-yl-pent-1-enyl)-5-oxo-cyclopentylsulfanyl]-propylsulfanyl}-acetic acid;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid methyl ester;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid methyl ester;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid methyl ester;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid methyl ester;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid methyl ester;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid;

{3-[(1R,2R)-2-((E)-3-Hydroxy-3-methyl-5-naphthalen-2-yl-pent-1-enyl)-5-oxo-cyclopentylsulfanyl]-propylsulfanyl}-acetic acid;

{3-[(1R,2R)-2-((E)-3-Hydroxy-5-naphthalen-2-yl-pent-1-enyl)-5-oxo-cyclopentylsulfanyl]-propylsulfanyl}-acetic acid methyl ester;

{3-[(1R,2R)-2-((E)-3-Hydroxy-5-naphthalen-2-yl-pent-1-enyl)-5-oxo-cyclopentylsulfanyl]-propylsulfanyl}-acetic acid methyl ester;

{3-[(1R,2R)-2-((E)-3-Hydroxy-5-naphthalen-2-yl-pent-1-enyl)-5-oxo-cyclopentylsulfanyl]-propylsulfanyl}-acetic acid;

{3-[(1R,2R)-2-((E)-3-Hydroxy-5-naphthalen-2-yl-pent-1-enyl)-5-oxo-cyclopentylsulfanyl]-propylsulfanyl}-acetic acid;

{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid methyl ester;

{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid methyl ester;

{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid;

{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid;

{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid methyl ester;

{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid methyl ester;

{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid;

{3-[(1R,2R)-2-((E)-3-Hydroxy-4-phenyl-but-1-enyl)-5-oxo-cyclopentylsulfanyl]-propylsulfanyl}-acetic acid methyl ester;

{3-[(1R,2R)-2-((E)-3-Hydroxy-4-phenyl-but-1-enyl)-5-oxo-cyclopentylsulfanyl]-propylsulfanyl}-acetic acid methyl ester;

{3-[(1R,2R)-2-((E)-3-Hydroxy-4-phenyl-but-1-enyl)-5-oxo-cyclopentylsulfanyl]-propylsulfanyl}-acetic acid;

{3-[(1R,2R)-2-((E)-3-Hydroxy-4-phenyl-but-1-enyl)-5-oxo-cyclopentylsulfanyl]-propylsulfanyl}-acetic acid;

{3-[(1R,2R)-2-((E)-3-Hydroxy-3-methyl-5-naphthalen-2-yl-pent-1-enyl)-5-oxo-cyclopentylsulfanyl]-propylsulfanyl}-acetic acid methyl ester;

{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid;

{3-[3-Hydroxymethyl-2-(3-hydroxy-4-phenyl-but-1-enyl)-5-oxo-cyclopentylsulfanyl]-propylsulfanyl}-acetic acid isopropyl ester;

{3-[(1R,2R)-2-((E)-(S)-3-Hydroxy-oct-1-enyl)-5-oxo-cyclopentylsulfanyl]-propylsulfanyl}-acetic acid;

{3-[(1R,2R)-2-((E)-3-Hydroxy-4-naphthalen-2-yl-but-1-enyl)-5-oxo-cyclopentylsulfanyl]-propylsulfanyl}-acetic acid;

{3-[(1R,2R)-2-((E)-3-Hydroxy-4-naphthalen-2-yl-but-1-enyl)-5-oxo-cyclopentylsulfanyl]-propylsulfanyl}-acetic acid methyl ester;

{3-[2-(4-Benzo[b]thiophen-3-yl-3-hydroxy-but-1-enyl)-5-oxo-cyclopentylsulfanyl]-propylsulfanyl}-acetic acid;

{3-[2-(4-Benzo[b]thiophen-3-yl-3-hydroxy-but-1-enyl)-5-oxo-cyclopentylsulfanyl]-propylsulfanyl}-acetic acid; and (3-{(1R,3R)-2-[(E)-5-(3-Chloro-benzo[b]thiophen-2-yl)-3-hydroxy-pent-1-enyl]-3-methyl-5-oxo-cyclopentylsulfanyl}-propylsulfanyl)-acetic acid methyl ester.

The compounds disclosed herein are useful for the prevention or treatment of glaucoma or ocular hypertension in mammals, or for the manufacture of a medicament for the treatment of glaucoma or ocular hypertension. They are also useful for the treatment of those diseases disclosed in the art as being amenable to treatment by prostaglandin $EP_4$ agonist, such as the ones listed previously.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, isobutyl, t-butyl, pentyl isomers, hexyl isomers, cyclopropyl, cyclobutyl, cyclopentyl, cyclohexyl, and combinations thereof having from 1–6 carbon atoms, etc.

Those skilled in the art will readily understand that for administration or the manufacture of medicaments the compounds disclosed herein can be admixed with pharmaceutically acceptable excipients which per se are well known in the art. Specifically, a drug to be administered systemically, it may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release. Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol and the like. In addition, if desired, the injectable pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician.

A liquid which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions of the present invention include, but are not limited to, benzalkonium chloride, chlorobutanol, thimerosal, phenylmercuric acetate and phenylmercuric nitrate. A useful surfactant is, for example, Tween 80. Likewise, various useful vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. A useful chelating agent is edetate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 1–10 |
| buffer | 0.01–10 |
| pH adjustor | q.s. pH 4.5–7.5 |
| antioxidant | as needed |
| surfactant | as needed |
| purified water | as needed to make 100% |

For topical use, creams, ointments, gels, solutions or suspensions, etc., containing the compound disclosed herein are employed. Topical formulations may generally be comprised of a pharmaceutical carrier, cosolvent, emulsifier, penetration enhancer, preservative system, and emollient.

Treatment of inflammatory bowel disease may be accomplished by the administration of the compounds described herein to the suffering mammal. Inflammatory bowel disease describes a variety of diseases characterized by inflammation of the bowels including, but not limited to, ulcerative colitis and Crohn's disease. Treatment may be accomplished by oral administration, by suppository, or parenteral administration, or some other suitable method.

While not intending to limit the scope of the invention in any way, delivery of the compounds disclosed herein to the colon via oral dosage forms may be accomplished by any of a number of methods known in the art. For example, reviews by Chourasia and Jain in *J Pharm Pharmaceut Sci* 6 (1): 33–66, 2003 and Shareef et. al (*AAPS Pharm Sci* 2003; 5 (2) Article 17) describe a number of useful methods. While not intending to limit the scope of the invention in any way these methods include 1) administration of a prodrug, including an azo or a carbohydrate based prodrug; 2) coating the drug with, or encapsulating or impregnating the drug into a polymer designed for delivery to the colon, 3) time released delivery of the drug, 4) use of a bioadhesive system; and the like.

While not intending to be bound in any way by theory, it is believed that intestinal microflora are capable of reductive cleavage of an azo bond leaving the two nitrogen atoms as amine functional groups. While not intending to limit the scope of the invention in any way, the azo prodrug approach has been used to deliver to 5-aminosalicylic acid humans in clinical trials for the treatment of irritable bowel disease. It is also believed that bacteria of the lower GI also have enzymes which can digest glycosides, glucuronides, cyclodextrins, dextrans, and other carbohydrates; and ester prodrugs formed from these carbohydrates have been shown to deliver the parent active drugs selectively to the colon. For example, in vivo and in vitro studies on rats and guinea pigs with prodrugs of dexamethasone, prednisolone, hydrocortisone, and fludrocortisone, suggest that glycoside conjugates may be useful for the delivery of steroids to the human colon. Other in vivo studies have suggested that glucuronide, cyclodextrin, and dextran prodrugs of steroids or non-steroidal anti-inflammatory drugs are useful for delivery of these drugs to the lower GI tract. An amide of salicylic acid and glutamic acid has been shown to be useful for the delivery of salicylic acid to the colon of rabbit and dog.

While not intending to limit the scope of the invention in any way, carbohydrate polymers such as amylase, arabinogalactan, chitosan, chondroiton sulfate, dextran, guar gum, pectin, xylin, and the like, or azo-group containing polymers can be used to coat a drug compound, or a drug may be impregnated or encapsulated in the polymer. It is believed that after oral administration, the polymers remain stable in the upper GI tract, but are digested by the microflora of the lower GI thus releasing the drug for treatment.

Polymers which are sensitive to pH may also be used since the colon has a higher pH than the upper GI tract. Such polymers are commercially available. For example, Rohm Pharmaceuticals, Darmstadt, Germany, markets pH dependent methacrylate based polymers and copolymers which have varying solubilities over different pH ranges based upon the number of free carboxylate groups in the polymer under the tradename Eudragit®. Several Eudragit® dosage forms are currently used to deliver salsalazine for the treatment of ulcerative colitis and Crohn's disease. Time release systems, bioadhesive systems, and other delivery systems have also been studied.

BIOLOGICAL ACTIVITY

The activity of compounds disclosed herein was tested according to the following procedures. The results are presented in Table 1.

Radioligand Binding

Cells Stably Expressing $EP_1$, $EP_2$, $EP_4$ and FP Receptors

HEK-293 cells stably expressing the human or feline FP receptor, or $EP_1$, $EP_2$, or $EP_4$ receptors were washed with TME buffer, scraped from the bottom of the flasks, and homogenized for 30 sec using a Brinkman PT 10/35 polytron. TME buffer was added to achieve a final 40 ml volume in the centrifuge tubes (the composition of TME is 100 mM TRIS base, 20 mM $MgCl_2$, 2M EDTA; 10N HCl is added to achieve a pH of 7.4).

The cell homogenate was centrifuged at 19000 r.p.m. for 20 min at 4° C. using a Beckman Ti-60 rotor. The resultant pellet was resuspended in TME buffer to give a final 1 mg/ml protein concentration, as determined by Biorad assay. Radioligand binding competition assays vs. [$^3$H-]17-phenyl $PGF_{2\alpha}$ (5 nM) were performed in a 100 µl volume for 60 min. Binding reactions were started by adding plasma membrane fraction. The reaction was terminated by the addition of 4 ml ice-cold TRIS-HCl buffer and rapid filtration through glass fiber GF/B filters using a Brandel cell harvester. The filters were washed 3 times with ice-cold buffer and oven dried for one hour. Non-specific binding was determined with 10 uM unlabeled 17-phenyl $PGF_{2\alpha}$.

[$^3$H-] $PGE_2$ (5 nM; specific activity 180 Ci mmol) was used as the radioligand for EP receptors. Binding studies employing $EP_1$, $EP_2$, $EP_3$, $EP_4$ were performed in duplicate in at least three separate experiments. A 200 μl assay volume was used. Incubations were for 60 min at 25° C. and were terminated by the addition of 4 ml of ice-cold 50 mM TRIS-HCl, followed by rapid filtration through Whatman GF/B filters and three additional 4 ml washes in a cell harvester (Brandel). Non-specific binding determined with $10^{-5}$ M of unlabeled $PGE_2$.

Methods for FLIPR™ Studies (a) Cell Culture

HEK-293 (EBNA) cells, stably expressing one type or subtype of recombinant human prostaglandin receptors (prostaglandin receptors expressed: hDP/Gqs5; $hEP_1$; $hEP_2$/Gqs5; $hEP_{3A}$/Gqi5; $hEP_4$/Gqs5; hFP; hIP; hTP), were cultured in 100 mm culture dishes in high-glucose DMEM medium containing 10% fetal bovine serum, 2 mM 1-glutamine, 250 μg/ml geneticin (G418) and 200 μg/ml hygromycin B as selection markers, and 100 units/ml penicillin G, 100 μg/ml streptomycin and 0.25 μg/ml amphotericin B.

(b) Calcium Signal Studies on the FLIPR™

Cells were seeded at a density of $5 \times 10^4$ cells per well in Biocoat® Poly-D-lysine-coated black-wall, clear-bottom 96-well plates (Becton-Dickinson) and allowed to attach overnight in an incubator at 37° C. Cells were then washed two times with HBSS-HEPES buffer (Hanks Balanced Salt Solution without bicarbonate and phenol red, 20 mM HEPES, pH 7.4) using a Denley Cellwash plate washer (Labsystems). After 45 minutes of dye-loading in the dark, using the calcium-sensitive dye Fluo-4 AM at a final concentration of 2 μM, plates were washed four times with HBSS-HEPES buffer to remove excess dye leaving 100 μl in each well. Plates were re-equilibrated to 37° C. for a few minutes.

Cells were excited with an Argon laser at 488 nm, and emission was measured through a 510–570 nm bandwidth emission filter (FLIPR™, Molecular Devices, Sunnyvale, Calif.). Drug solution was added in a 50 μl volume to each well to give the desired final concentration. The peak increase in fluorescence intensity was recorded for each well. On each plate, four wells each served as negative (HBSS-HEPES buffer) and positive controls (standard agonists: BW245C (hDP); $PGE_2$ ($hEP_1$; $hEP_2$/Gqs5; $hEP_{3A}$/Gqi5; $hEP_4$/Gqs5); $PGF_{2\alpha}$ (hFP); carbacyclin (hIP); U46619 (hTP), depending on receptor). The peak fluorescence change in each drug-containing well was then expressed relative to the controls.

Compounds were tested in a high-throughput (HTS) or concentration-response (CoRe) format. In the HTS format, forty-four compounds per plate were examined in duplicates at a concentration of $10^{-5}$ M. To generate concentration-response curves, four compounds per plate were tested in duplicates in a concentration range between $10^{-5}$ and $10^{-11}$ M. The duplicate values were averaged. In either, HTS or CoRe format each compound was tested on at least 3 separate plates using cells from different passages to give an $n \geq 3$.

TABLE 1

| STRUCTURE | Stereo Chem | BINDING IC$_{50}$ (NM) ||||||| FUNCTIONAL EC$_{50}$ (NM) |||||||
|---|---|---|---|---|---|---|---|---|---|---|---|---|---|---|
| | | FP | HEP2 | HEP3D | HEP4 | HFP | HEP1 | HEP2 | HEP3A | HEP4 | HTP | HIP | HDP |
| (structure 1) | Low Rf Diast. | NA | NA | NA | 96 | NA | | | >10000 | 1.8 | >10000 | NA | |
| (structure 2) | Low Rf Diast. | >10000 | >10000 | >10000 | 44 | NA | | | 1950 | 3.7 | >10000 | NA | |
| (structure 3) | High Rf Diast. | >10000 | >10000 | | 45 | NA | | | NA | 2.4 | NA | NA | |
| (structure 4) | High Rf Diast. | NA | | | 300 | NA | | | NA | 7.8 | NA | NA | |

TABLE 1-continued
| STRUCTURE | Stereo Chem | BINDING IC$_{50}$ (NM) | | | | FUNCTIONAL EC$_{50}$ (NM) | | | | | | |
| --- | --- | --- | --- | --- | --- | --- | --- | --- | --- | --- | --- | --- |
| | | FP | HEP2 | HEP3D | HEP4 | HFP | HEP1 | HEP2 | HEP3A | HEP4 | HTP | HIP | HDP |
| 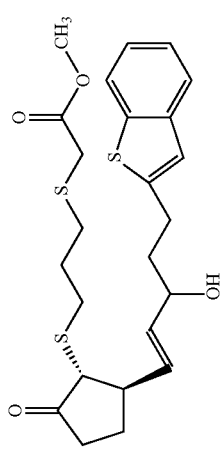 | Low Rf Diast. | | >10000 | | 300 | NA | | | NA | 11 | NA | NA | |
| 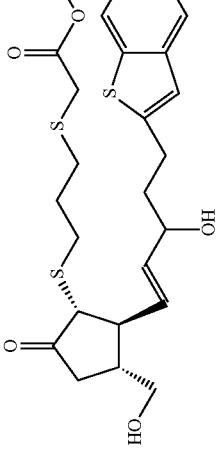 | High Rf Diast. | | NA | | 2100 | NA | | | NA | 7943 | NA | NA | |
| 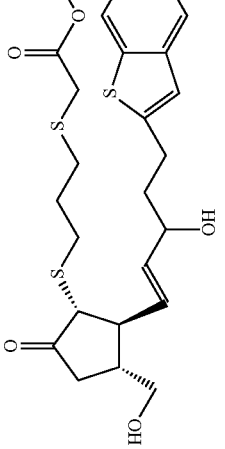 | Low Rf Diast. | | NA | | 1900 | NA | | | NA | >10000 | NA | NA | |
| 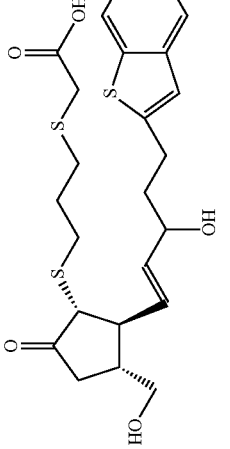 | High Rf Diast. | | NA | | 1300 | NA | | | NA | 363 | NA | NA | |

TABLE 1-continued
| STRUCTURE | Stereo Chem | BINDING IC$_{50}$ (NM) | | | | FUNCTIONAL EC$_{50}$ (NM) | | | | | | |
| --- | --- | --- | --- | --- | --- | --- | --- | --- | --- | --- | --- | --- |
| | | FP | HEP2 | HEP3D | HEP4 | HFP | HEP1 | HEP2 | HEP3A | HEP4 | HTP | HIP | HDP |
| 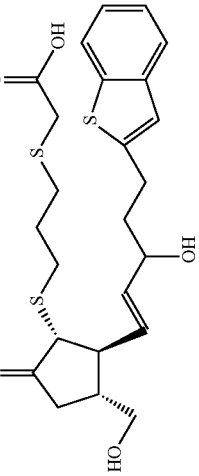 | Low Rf Diast. | | NA | | 100 | NA | | | NA | 463 | NA | NA | |
| 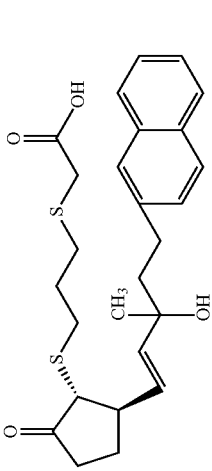 | High Rf Diast. | | NA | | 200 | NA | | | NA | 20 | >10000 | NA | |
| 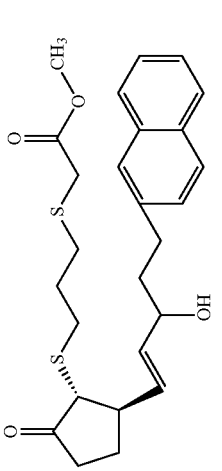 | High Rf Diast. | | NA | | 300 | NA | | | NA | 0.5 | NA | NA | |
| 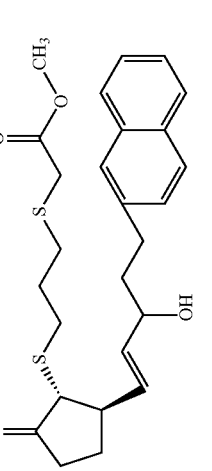 | Low Rf Diast. | | NA | | 200 | NA | | | NA | 0.6 | NA | NA | |

TABLE 1-continued

| STRUCTURE | Stereo Chem | BINDING IC$_{50}$ (NM) | | | | FUNCTIONAL EC$_{50}$ (NM) | | | | | |
| --- | --- | --- | --- | --- | --- | --- | --- | --- | --- | --- | --- |
| | | FP | HEP2 | HEP3D | HEP4 | HFP | HEP1 | HEP2 | HEP3A | HEP4 | HTP | HIP | HDP |
| (structure) | High Rf Diast. | | 8100 | | 140 | NA | | | NA | 1 | NA | NA | |
| (structure) | Low Rf Diast. | | >10000 | | 140 | NA | | | >10000 | 0.3 | >10000 | NA | |
| (structure) | High Rf Diast. | | NA | | 1600 | NA | | | NA | 2344 | NA | NA | |
| (structure) | 1 | | NA | | 140 | NA | | | NA | 1862 | NA | >10000 | |

TABLE 1-continued

| STRUCTURE | Stereo Chem | BINDING IC$_{50}$ (NM) | | | | FUNCTIONAL EC$_{50}$ (NM) | | | | | | | |
|---|---|---|---|---|---|---|---|---|---|---|---|---|
| | | FP | HEP2 | HEP3D | HEP4 | HFP | HEP1 | HEP2 | HEP3A | HEP4 | HTP | HIP | HDP |
| (naphthyl carboxylic acid structure) | High Rf Diast. | | NA | | 1000 | NA | NA | NA | NA | 465 | NA | NA | |
| (naphthyl carboxylic acid structure) | Low Rf Diast. | | NA | | 400 | NA | NA | NA | NA | 219 | NA | NA | NA |
| (phenyl methyl ester structure) | Low Rf Diast. | | NA | | 195 | NA | NA | NA | NA | 106 | NA | NA | NA |
| (phenyl methyl ester structure) | High Rf Diast. | | NA | | 1050 | NA | NA | NA | NA | 2089 | NA | NA | NA |

TABLE 1-continued

| STRUCTURE | Stereo Chem | BINDING IC$_{50}$ (NM) | | | | | FUNCTIONAL EC$_{50}$ (NM) | | | | | | |
|---|---|---|---|---|---|---|---|---|---|---|---|---|---|
| | | FP | HEP2 | HEP3D | HEP4 | HFP | HEP1 | HEP2 | HEP3A | HEP4 | HTP | HIP | HDP |
| (cyclopentanone with S-CH2-COOH chain and styryl-CHOH-CH2OH) | Low Rf Diast. | | NA | >10000 | 53 | NA | NA | NA | NA | 59 | NA | NA | NA |
| (cyclopentanone with S-CH2-COOCH3 chain and styryl-CHOH) | High Rf Diast. | | NA | NA | 141 | NA | NA | NA | NA | 15 | NA | NA | NA |
| (cyclopentanone with S-CH2-COOCH3 chain and styryl-CHOH) | Low Rf Diast. | | NA | >10000 | 19 | NA | NA | NA | >10000 | 0.09 | >10000 | NA | |
| (cyclopentanone with S-CH2-COOH chain and styryl-CHOH) | High Rf Diast. | | NA | >10000 | 55 | NA | NA | NA | >10000 | 60 | NA | | |

TABLE 1-continued

| STRUCTURE | Stereo Chem | BINDING IC$_{50}$ (NM) | | | | FUNCTIONAL EC$_{50}$ (NM) | | | | | | | |
| --- | --- | --- | --- | --- | --- | --- | --- | --- | --- | --- | --- | --- | --- |
| | | FP | HEP2 | HEP3D | HEP4 | HFP | HEP1 | HEP2 | HEP3A | HEP4 | HTP | HIP | HDP |
| (structure) | Low Rf Diast. | | NA | >10000 | 11 | NA | NA | NA | >10000 | >10000 | >10000 | NA | NA |
| (structure) | Low Rf Diast. | | NA | | 500 | NA | NA | NA | NA | 46 | NA | NA | |
| (structure) | High Rf Diast. | | NA | | 440 | NA | NA | NA | NA | 135 | NA | NA | NA |
| (structure) | Low Rf Diast. | | | | | | | | | | | | |

TABLE 1-continued

| STRUCTURE | Stereo Chem | BINDING IC$_{50}$ (NM) | | | | FUNCTIONAL EC$_{50}$ (NM) | | | | | | |
|---|---|---|---|---|---|---|---|---|---|---|---|---|
| | | FP | HEP2 | HEP3D | HEP4 | HFP | HEP1 | HEP2 | HEP3A | HEP4 | HTP | HIP | HDP |
| (structure) | | | 2200 | | 20 | NA | >10000 | 1223 | 16 | 1.6 | | NA | >10000 |
| (structure) | Low Rf Diast.. | | NA | >10000 | 26 | NA | NA | NA | NA | 0.4 | >10000 | NA | |
| (structure) | Low Rf Diast.. | | NA | >10000 | 83 | NA | NA | NA | NA | | NA | NA | |
| (structure) | Low Rf Diast.. | | 600 | >10000 | 26 | NA | NA | >10000 | >10000 | 7244 | 3.7 | 389 | NA |

TABLE 1-continued

| STRUCTURE | Stereo Chem | BINDING IC$_{50}$ (NM) | | | | FUNCTIONAL EC$_{50}$ (NM) | | | | | | |
| --- | --- | --- | --- | --- | --- | --- | --- | --- | --- | --- | --- | --- |
| | | FP | HEP2 | HEP3D | HEP4 | HFP | HEP1 | HEP2 | HEP3A | HEP4 | HTP | HIP | HDP |
| [structure] | High Rf Diast. | | 3500 | >10000 | NA | NA | NA | >10000 | >10000 | 6.8 | >10000 | NA | |

In Vivo Testing

Intraocular Pressure (IOP)

Intraocular pressure studies in dogs involved pneumatonometry performed in conscious, Beagle dogs of both sexes (10–15 kg). The animals remained conscious throughout the study and were gently restrained by hand. Drugs were administered topically to one eye as a 25 µL volume drop, the other eye received 25 µL vehicle (0.1% polysorbate 80:10 mM TRIS) as a control. Proparacaine (0.1%) was used for corneal anesthesia during tonometry. Intraocular pressure was determined just before drug administration and at 2, 4 and 6 hr thereafter on each day of the 5 day study. Drug was administered immediately after the first IOP reading.

An analogous procedure was carried out with cynomolgus monkeys with measurements at 2, 4, 6, and 24 hours after a single dose.

Pupil Diameter

Dog pupil diameter was measured using an optistick (a mm ruler which included half-circle references of standard widths (mm) for reference. Gently restraining the dog by hand, pupil diameter was determined by matching a half-circle to the pupil in normal room light. In dogs with very dark pupils a specialized penlight was used, but only very briefly to avoid pupil constriction. Pupil diameter was measured at the same time as IOP and hyperemia.

Ocular Surface Hyperemia

Ocular surface hyperemia was visually assessed and scored according to a system typically used clinically.

| Hyperemia Score | Assigned Value |
| --- | --- |
| <1 trace | 0.5 |
| 1 mild | 1 |
| moderate | 2 |
| severe | 3 |

Ocular surface hyperemia was evaluated at the same time points as intraocular pressure measurement. It should be noted that untreated dog eyes frequently have a pink/red tone. Thus, values of trace or even mild are not necessarily out of the normal range.

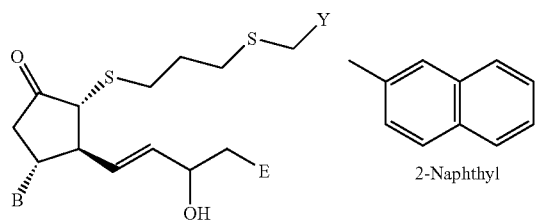

Testing was carried out with the compounds described by the structure above and Table 2 below. Results are presented in Table 3.

TABLE 2

| Compound | Diastereomer | B | E | Y |
| --- | --- | --- | --- | --- |
| 150 | Low Rf | CH$_2$OH | Phenyl | CO$_2$CH(CH$_3$)$_2$ |
| 151 | Low Rf | CH$_2$OH | Phenyl | CO$_2$H |
| 141b | Low Rf | CH$_2$OH | CH$_2$-(2-Naphthyl) | CO$_2$H |
| 153 | Low Rf | H | CH$_2$-(2-Naphthyl) | CO$_2$H |

TABLE 3

| | | DOG | | | MONKEY | |
| --- | --- | --- | --- | --- | --- | --- |
| Compound | Conc. | n | Max. ΔIOP (mm Hg) | Max hyperemia | n | Max. ΔIOP (mm Hg) |
| 141b | 0.1% | 8 | −1.6 | 0.7 | | |
| 150 | 0.03% | 8 | −5.5 | 0.9 | | |
| 151 | 0.1% | 8 | −4.0 | 1.6 | 10 | −2.9 |
| 153 | 0.1% | 8 | −4.4 | 1.8 | | |

Synthetic Procedures (3-Chloro-benzo[b]thiophen-2-yl)-methanol (2). To an ice cold solution of 10.0 g (47.0 mmol) of 3-chloro-benzo[b]thiophene-2-carboxylic acid (1) in 200 mL of THF was added 47 mL of LiAlH$_4$ (47 mmol, 1 M/THF). After 3 h, the reaction was quenched by addition of MeOH (ca. 40 mL). The volatiles were evaporated and the residue was treated with 50 mL 1 M HCl. After stirring for 10 min., the mixture was extracted with CH$_2$Cl$_2$ (3×150 mL). The combined CH$_2$Cl$_2$ solution was dried (MgSO$_4$), filtered and evaporated. Purification by flash chromatography on silica gel (10→20% ethyl acetate/hexane) gave 4.32 g (21.6 mmol, 46%) of the alcohol (2).

3-Chloro-benzo[b]thiophene-2-carbaldehyde (3). A solution of alcohol 2 (4.32 g, 21.6 mmol) in 40 mL of CH$_2$Cl$_2$ was treated with 4A molecular sieves, NMO (3.81 g, 32.5 mmol), and TPAP (381 mg, 1.08 mmol). The reaction was stirred for 10 min. and then was evaporated to dryness. Purification by flash chromatography on silica gel (2% ethyl acetate/hexane) gave 3.52 g (18.3 mmol, 84%) of the aldehyde (3).

(E)-3-(3-Chloro-benzo[b]thiophen-2-yl)-acrylic acid methyl ester (4). A solution of 3.52 g (18.3 mmol) of 3 in 50 mL toluene was treated with methyl(triphenylphosphoranylidene)acetate (7.48 g, 21.9 mmol). After 4 h, saturated NaHCO$_3$ solution (50 mL) was added and the mixture was extracted with ethyl acetate (2×75 mL). The combined ethyl acetate solution was washed with brine (50 mL), dried (Na$_2$SO$_4$), filtered and evaporated. Purification by flash chromatography on silica gel (5% ethyl acetate/hexane) provided 3.60 g (14.6 mmol, 80%) of the enoate (4).

3-(3-Chloro-benzo[b]thiophen-2-yl)-propionic acid methyl ester (5). A solution of 3.60 g (14.6 mmol) of 4 in 50 mL THF was treated with Wilkinson's catalyst (3.35 g, 3.62 mmol). The mixture was stirred under 1 atm H$_2$ for 18 h and then was filtered through celite. The solvent was evaporated and the residue was purified by flash chromatography on silica gel (0→2% ethyl acetate/hexane) to give 3.63 g (14.3 mmol, 99%) of the saturated ester (5).

3-(3-Chloro-benzo[b]thiophen-2-yl)-propan-1-ol (6). An ice cold solution of 3.63 g (14.3 mmol) of 5 in 60 mL of ether was treated with LiBH$_4$ (621 mg, 28.5 mmol) and methanol (2 mL). After 30 min., 30 mL of 0.5 M NaOH solution was added. The mixture was extracted with ethyl acetate (2×25 mL) and the combined ethyl acetate solution was washed with brine (50 mL), dried (MgSO$_4$), filtered and evaporated. The residue was purified by flash chromatography on silica gel (5→20% ethyl acetate/hexane) to give 2.57 g (11.3 mmol, 79%) of the alcohol (6).

3-(3-Chloro-benzo[b]thiophen-2-yl)-propionaldehyde (7). A −78° C. solution of oxalyl chloride (1.73 g, 13.6 mmol) in dichloromethane (20 mL) was treated with DMSO (20 mL). After 5 min., a solution of alcohol 6 (2.57 g, 11.3 mmol) in dichloromethane (20 mL) was added. After another 15 min., triethylamine (7.1 mL, 50.6 mmol) was added. The reaction was stirred at −78° C. for 5 min., and then was allowed to warm to room temperature. After 30 min., 100 mL water was added and the mixture was extracted with dichloromethane (3×60 mL). The combined dichloromethane solution was dried (Na$_2$SO$_4$), filtered and evaporated. Purification by flash chromatography on silica gel (10% ethyl acetate/hexane) gave 2.11 g (9.4 mmol, 83%) of the aldehyde (7).

5-(3-Chloro-benzo[b]thiophen-2-yl)-pent-1-yn-3-ol (8). A solution of aldehyde 7 (2.11 g, 9.4 mmol) in 15 mL THF was added to a solution of ethynylmagnesium bromide (28.2 mL, 14.1 mmol, 0.5 M THF) at 0° C. After 1.5 h, saturated NH$_4$Cl solution (75 mL) was added and the mixture was extracted with ethyl acetate (3×50 mL). The combined ethyl acetate solution was washed with brine (50 mL) and then was dried (Na$_2$SO$_4$), filtered and evaporated. Purification by flash chromatography (5→20% ethyl acetate/hexane) gave 2.20 g (8.78 mmol, 93%) of the alcohol (8).

tert-Butyl-{1-[2-(3-chloro-benzo[b]thiophen-2-yl)-ethyl]-prop-2-ynyloxy}-dimethyl-silane (9). A solution of alcohol 8 (2.20 g, 8.78 mmol) in dichloromethane (15 mL) was treated with DMAP (215 mg, 1.8 mmol), TBSCl (1.59 g, 10.5 mmol), and triethylamine (1.8 mL, 13.2 mmol). The reaction was stirred for 24 h and then saturated sodium bicarbonate solution (50 mL) was added. The mixture was extracted with dichloromethane (2×50 mL) and the combined dichloromethane solution was dried (Na$_2$SO$_4$), filtered and evaporated. Purification by flash chromatography (4% ethyl acetate/hexane) gave 3.06 g (6.4 mmol, 73%) of the protected alcohol (9).

(3-{(1R,3R)-3-(tert-Butyl-dimethyl-silanyloxy)-2-[(E)-3-(tert-butyl-dimethyl-silanyloxy)-5-(3-chloro-benzo[b]thiophen-2-yl)-pent-1-enyl]-5-oxo-cyclopentylsulfanyl}-propylsulfanyl)-acetic acid methyl ester (11). Cp$_2$ZrHCl (103 mg, 0.40 mmol) was added to a solution of alkyne 9 (120 mg, 0.33 mmol) in 1 mL THF. After 1 h, the solid had dissolved and the resulting yellow solution was cooled to −78° C. MeLi (0.52 mL, 0.73 mmol, 1.4 M/ether) was added and the reaction was stirred for 15 min. 2-Thienyl-CuCNLi (1.46 mL, 0.37 mmol, 0.25 M/THF) was then added and the mixture was stirred for 30 min. further. At this time, a solution of enone 10 (109 mg, 0.28 mmol), prepared according to U.S. Pat. No. 6,043,275, expressly incorporated by reference herein, in 5 mL THF was added dropwise by cannula, rinsing with 0.2 mL THF. The reaction was stirred for 2 h and then was quenched by addition of 10% concentrated NH$_4$OH (aq)/saturated NH$_4$Cl(aq) (20 mL). The mixture was stirred for 15 min. and then was extracted with ethyl acetate (3×20 mL). The combined ethyl acetate solution was dried (Na$_2$SO$_4$), filtered and evaporated. Purification by flash chromatography on silica gel (10% ethyl acetate/hexanes→15%) gave the title ketone (83 mg, 0.11 mmol, 39%).

(3-{(1R,4R)-2-(tert-Butyl-dimethyl-silanyloxy)-5-[(E)-3-(tert-butyl-dimethyl-silanyloxy)-5-(3-chloro-benzo[b]thiophen-2-yl)-pent-1-enyl]4-hydroxy-cyclopent-2-enyl-sulfanyl}-propylsulfanyl)-acetic acid methyl ester (12). Et$_3$N (0.86 mL, 6.2 mmol) and TBSOTf (0.69 mL, 3.5 mmol) were added to a dichloromethane (20 mL) solution of ketone 11 (569 mg, 0.75 mmol). After 1 h, 65 mL saturated NaHCO$_3$ solution ws added and the resulting mixture was extracted with dichloromethane (20 mL). The dichloromethane solution was washed with H$_2$O (50 mL) and then was dried ((Na$_2$SO$_4$), filtered and evaporated. Purification by flash chromatography on silica gel (8% ethyl acetate/hexanes) gave 12 (576 mg, 0.66 mmol, 88%) as a dark oil.

(3-{(R)-2-[(E)-3-(tert-Butyl-dimethyl-silanyloxy)-5-(3-chloro-benzo[b]thiophen-2-yl)-pent-1-enyl]-5-oxo-cyclopent-3-enylsulfanyl}-propylsulfanyl)-acetic acid methyl ester (13). Amberlyst 15 resin (255 mg) was added to a solution of enol silane 12 (576 mg, 0.66 mmol) in dichloromethane (20 mL). The mixture was stirred for 2 h and then was filtered and evaporated. Purification by flash chromatography on silica gel (10% ethyl acetate/hexanes→15%) gave the title compound (131 mg, 0.21 mmol, 28%).

(3-{(1R,3R)-2-[(E)-5-(3-Chloro-benzo[b]thiophen-2-yl)-3-hydroxy-pent-1-enyl]-3-methyl-5-oxo-cyclopentylsulfanyl}-propylsulfanyl)-acetic acid methyl ester (14). MeLi (0.57 mL, 0.80 mmol, 1.4 M/ether) was added to a −78° C. mixture of CuCN (45 mg, 0.50 mmol) in THF (0.5 mL). The mixture was stirred for 5 min. at −78° C. and then was allowed to warm to room temperature. After 10 min. at room temperature, the mixture was cooled back down to −78° C. At this time, a solution of enone 13 (76 mg, 0.12 mmol) in 0.5 mL THF was added dropwise by cannula, rinsing with 0.25 mL THF. The reaction was stirred for 30 min. and then was quenched by addition of 10 mL saturated NH$_4$Cl solution. The resulting mixture was stirred for 10 min. at room temperature and then was extracted with ethyl acetate (3×15 mL). The combined ethyl acetate solution was dried (MgSO$_4$), filtered and evaporated.

The crude ketone was dissolved in 3.3 mL CH$_3$CN and HF-pyridine (0.54 mL) was added. The reaction was stirred for 4 h at which time 30 mL saturated NaHCO$_3$ was added. The mixture was extracted with dichloromethane (3×20 mL) and the combined dichloromethane solution was dried (MgSO$_4$), filtered and evaporated. Purification by preparative thin layer chromatography on silica gel (35% ethyl acetate/hexanes) gave 10 mg each (0.020 mmol, 25%) of the two C15 diastereomers of compound 14.

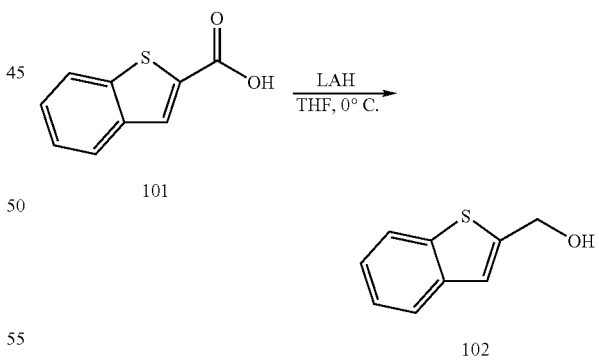

Lithium aluminum hydride (22.4 mmole, 22.4 ml) was added to a solution of 101 (2.0 g, 11.2 mmole) in THF (100 ml) at 0° C. After 5 minutes, the mixture was warmed to room temperature and stirred for 2 hours. The mixture was then cooled to 0° C., and MeOH (1 ml) was added slowly until no gas was evolved, followed by the addition of 1NHCl. After stirring for 30 min at room temperature, the mixture was concentrated in vacuo, diluted in 1N HCl, and extracted with EtOAc (×3). The combined organics were washed with brine, dried (Na$_2$SO$_4$), concentrated in vacuo and dried over pump for 16 hours to give 1.8 g of crude 102.

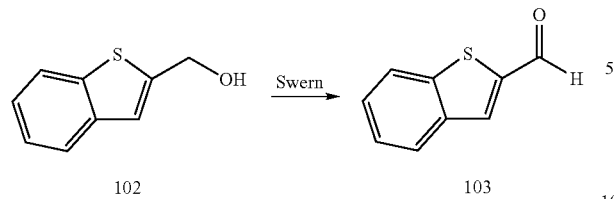

Dimethyl sulfoxide (3.2 ml, 44.8 mmol) was added dropwise to a solution of oxayl chloride (11.2 ml, 22.4 mmol) in DCM (150 ml) at −78° C. After string for 30 minutes, a solution of crude 2 (1.8 g) in DCM (50 ml) was added and stirred for 1 hour at −78° C. To the resulting mixture, triethylamine (12.4 ml, 89.6 mmole) was added and the mixture was allowed to warmed to room temperature. After 1 hour, the mixture was poured into saturated aqueous $NaHCO_3$ and extracted with DCM (×3). The combined organics were washed with brine, dried ($NaSO_4$), concentrated in vacuo and purified by flash column chromatography (100% DCM) to give 1.8 g of pure 103.

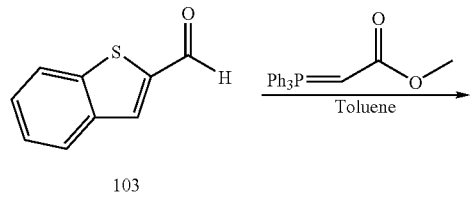

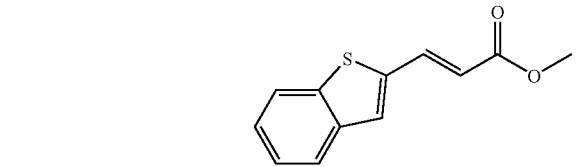

Methyl(triphenyl phosphoranylidene)acetate (8.5 g, 25.3 mmole) was added to a solution of 3 (2.1 g, 12.9 mmole) in toluene (200 ml). After 2 days at room temperature, the mixture was concentrated in vacuo and the crude was loaded on a pack of silica gel in suction filter and washed with a solvent (8/1: hexane/EtOAc). The combined organics were concentrated in vacuo to give 3.0 g of 104.

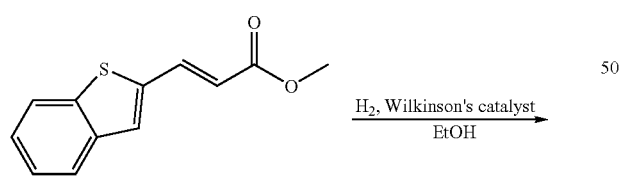

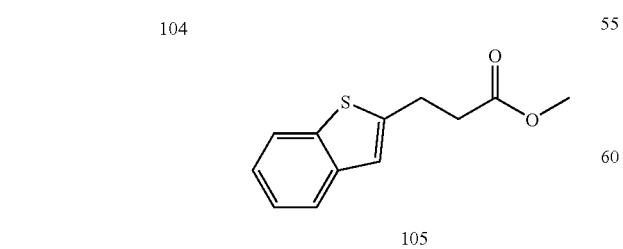

Chlorotris(triphenyl phosphine)rhodium (1.2 g, 1.3 mmole) was added to a solution of 104 (3.0 g, 0.013 mole) in EtOH (100 ml). The mixture was charged with $H_2$ and stirred at room temperature for 16 hours. The mixture was then concentrated in vacuo and purified by flash column chromatography (9/1: hexane/EtOAc) to give 3.0 g of 105.

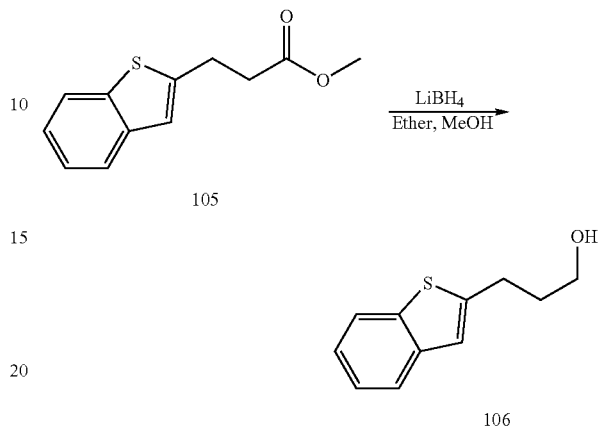

Lithium borohydride (0.57 g, 0.026 mole) was added to a solution of 105 (3.0 g, 0.013 mole) in ether (100 ml) at 0° C., followed by the addition of MeOH (0.83 g, 0.026 mole). The mixture was then warmed to room temperature and stirred for 3 hours. After TLC indicated no starting materials, the mixture was cooled to 0° C. and aqueous solution of NaOH was added dropwise. After 1 hour of stirring, the mixture was combined with brine and extracted with EtOAc (×3). The combined organics were washed with brine, dried ($Na_2SO_4$), concentrated in vacuo, and purified by flash column chromatography (100% DCM) to give 2.5 g of 106.

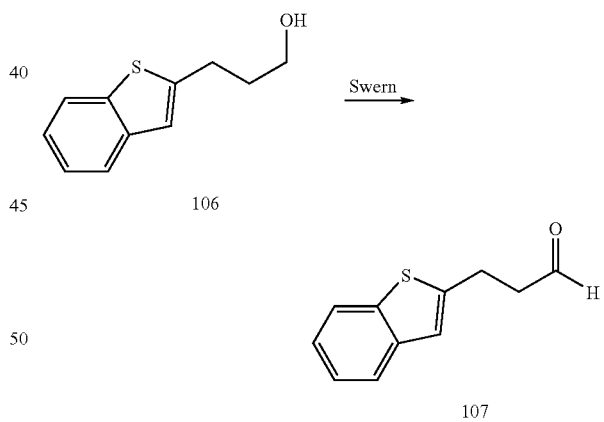

Dimethyl sulfoxide (3.7 ml, 52 mmole) was added dropwise to a solution of oxayl chloride (13 ml, 26 mmole) in DCM (150 ml) at −78° C. After 5 minutes, a solution of 106 (2.5 g, 13 mmole) in DCM (40 ml) was added and stirred for 1 hour at −78° C. After the addition of triethylamine (10.5 g, 110 mmole), the mixture was warmed to room temperature over 1 hour, poured into saturated $NaHCO_3$, and extracted with DCM (×3). The combined organics were washed with brine, dried ($Na_2SO_4$), concentrated in vacuo and purified by flash column chromatography (100% DCM) to give 2.6 g of 107.

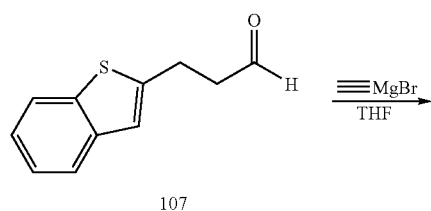

107

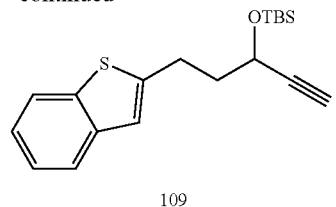

109

Tert-butyldimethyltrifluromethanesalformate (5.4 g, 20.4 mmole) was added to a mixture of crude 108 and triethylamine (4.1 g, 40.8 mmole) in DCM (20 ml) at 0° C. After 1 hour at room temperature, NaHCO$_3$ was added and the solvent was removed in vacuo. Flash column chromatography (100% hexane→2/1: hexane/DCM) gave 2.2 g of 109.

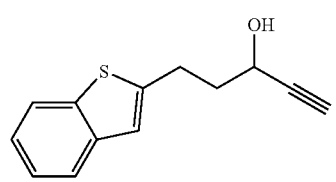

108

Ethynylmagunesium bromide (54.7 ml, 27.2 mmole) was added to a solution of 7 (1.3 g, 6.8 mmole) in THF (100 ml) at 0° C. The mixture was warmed to room temperature over 16 hours, quenched with saturated aqueous NH$_4$Cl and concentrated in vacuo. The crude was diluted with NH$_4$Cl and extracted with EtOAc (×3). The combined organics were washed with brine, dried (Na$_2$SO$_4$) and concentrated in vacuo to give crude 108.

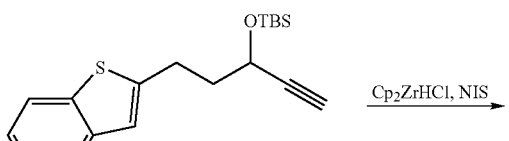

109

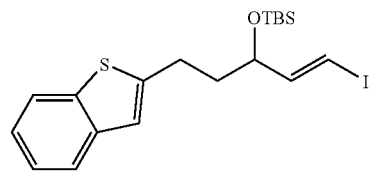

110

Bis(cyclopentadienyl)zirconium chloride hydride (2.1 g, 8.2 mmole) was added to a solution of 109 (2.2 g, 6.8 mmole) in DCM (100 ml). After 20 minutes, N-iodosuccimide (1.8 g, 8.2 mole) was added and stirred for additional 30 minutes. The mixture was then concentrated in vacuo (~10 ml of solvent) and loaded on flash column chromatography (100% hexane). The concentrated product was diluted with hexane, washed with sodium bisulfite (×2), brine, dried (Na$_2$SO$_4$), concentrated in vacuo, and purified by flash column chromatography (100% hexane) to give 1.5 g of 110.

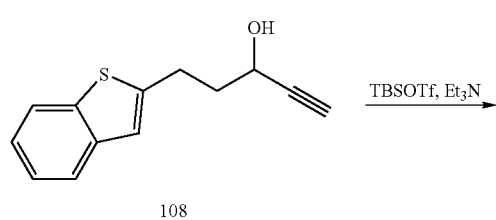

108

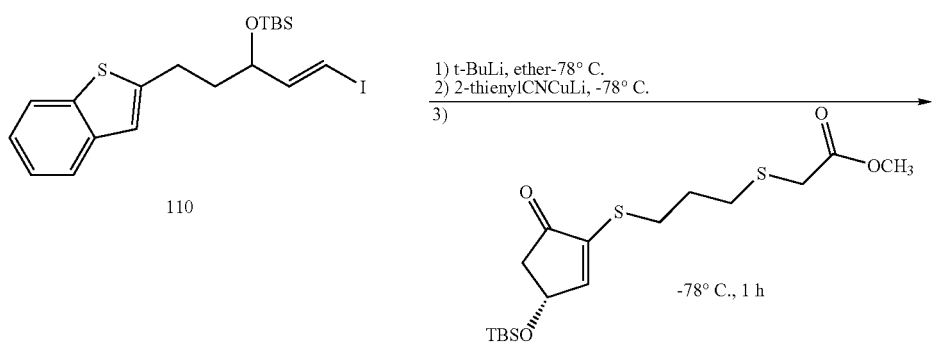

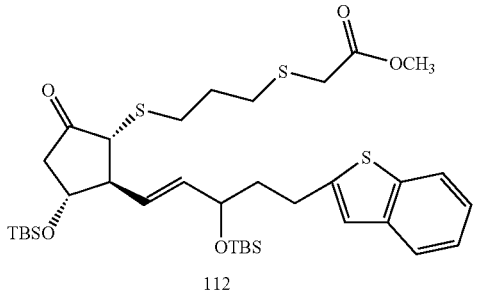

112

Tert-Butyl lithium (1.62 mmole, 0.95 ml) was added to a solution of 110 (370 mg, 0.81 mmole) in ether (2 ml) at −78° C. After 30 min, 2-thienylcyanocuprate lithium (0.94 mmole, 3.76 ml) was added to the mixture and stirred for 30 minutes, at which point, a solution of 10 (310 mg, 0.78 mole) in ether (1 ml) was added to the mixture. After stirring for one hour at −78° C., the mixture was quenched with saturated aqueous NH₄Cl and extracted with EtOAc (×3). The combined organics were washed with brine, dried (Na₂SO₄), concentrated in vacuo, and purified by flash column chromatography (9/1: hexane/EtOAc) to give 250 mg of 112.

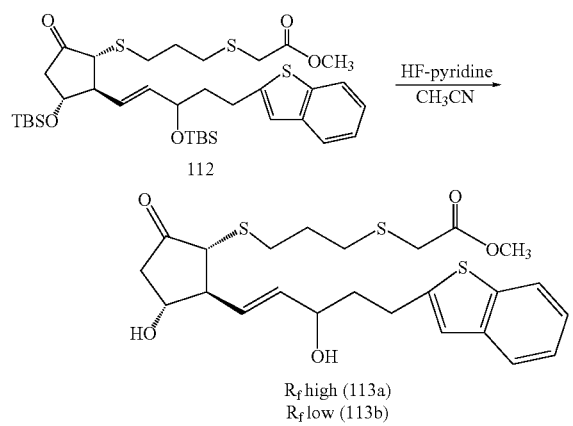

R$_f$ high (113a)
R$_f$ low (113b)

HF-pyridine (340 ul) was added to a solution of 112 (250 mg, 0.34 mmole) in MeCN (3 ml). After 2 hours at room temperature, the mixture was quenched with NaHCO₃ and extracted with EtOAc (×3). The combined organics were washed with brine, dried (Na₂SO₄), concentrated in vacuo, and purified by preparative TLC (Whatman PK6F silica gel 60 Å°, 1000 um, 2% MeOH/DCM).

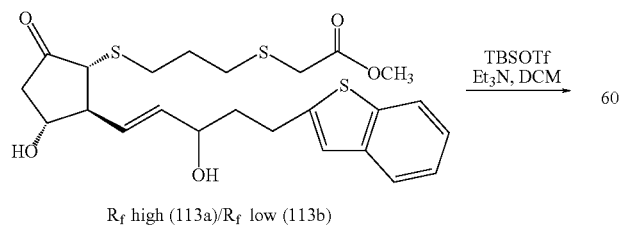

R$_f$ high (113a)/R$_f$ low (113b)

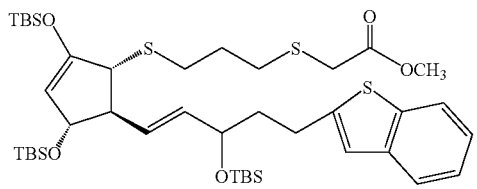

R$_f$ high (114a)/R$_f$ low (114b)

Tert-butyldimethyl trifluoromethanesulformate (94 mg, 0.35 mmole) was added to a mixture of 113a (44 mg, 0.089 mmole) and triethylamine (71 mg, 0.71 mmole) in DCM (3 ml) at 0° C. After 30 minutes stirring at room temperature, the mixture was quenched with NaHCO₃ and extracted with DCM (×3). The combined organics were washed with brine, dried (Na₂SO₄), concentrated in vacuo and purified by flash column chromatography (5% EtOAc/Hexane) to give 33 mg of 114a.

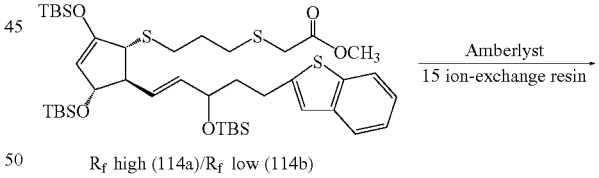

R$_f$ high (114a)/R$_f$ low (114b)

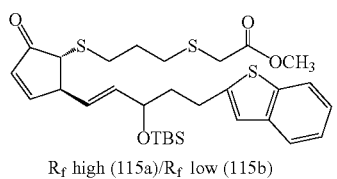

R$_f$ high (115a)/R$_f$ low (115b)

Amberlyst was added to a solution of 114a (33 mg, 0.039 mmole) in DCM (3 ml). After 3 hours stirring at room temperature, the mixture was loaded on flash column chromatography (9/1: hexane/EtOAc→4/1: hexane/EtOAc) to give 9.0 mg of 115a.

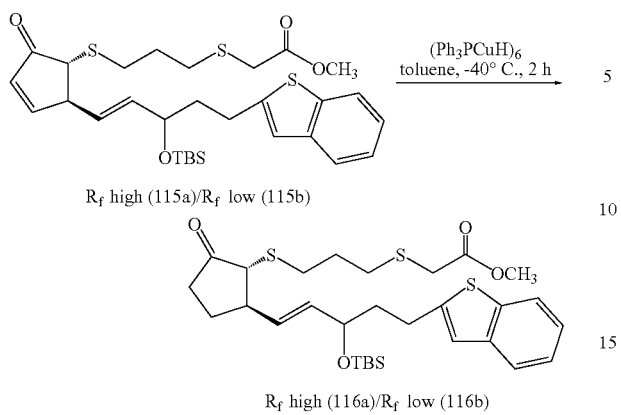

R$_f$ high (115a)/R$_f$ low (115b)

R$_f$ high (116a)/R$_f$ low (116b)

A solution of 115a (9.0 mg, 0.015 mmole) in toluene (1 ml) was added to a solution of Stryker's reagent (45 mg, 0.023 mmole) in toluene (5 ml) at −40° C. After stirring for 2 hours at −40° C., the mixture was quenched with NH$_4$OH/NH$_4$Cl (1/1) and stirred for 30 minutes until it became blue solution. The mixture was extracted with EtOAc (×1)+DCM (×2), and combined organics were washed with brine, dried (Na$_2$SO$_4$), concentrated in vacuo and purified by flash column chromatography (9/1: hexane/EtOAc→4/1: hexane/EtOAc) to give 7.5 mg of 116a.

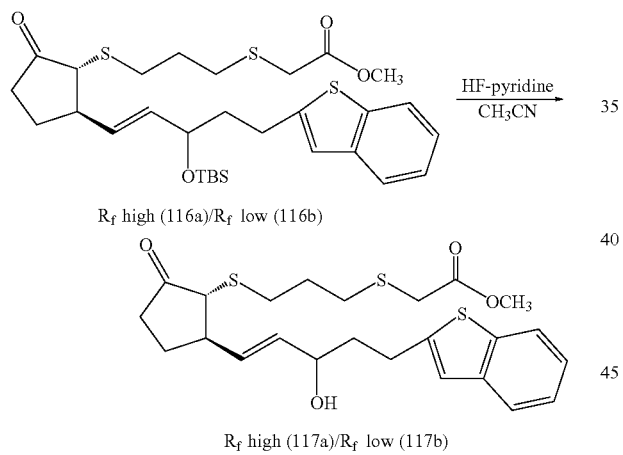

R$_f$ high (116a)/R$_f$ low (116b)

R$_f$ high (117a)/R$_f$ low (117b)

HF-pyridine (13 ul) was added to a solution of 116a (7.5 mg, 0.013 mmole) in MeCN (2 ml). After 2 hours at room temperature, the mixture was quenched with NAHCO$_3$ and extracted with EtOAc (×3). The combined organics were washed with brine, dried (Na$_2$SO$_4$), concentrated in vacuo, purified by flash column chromatography (4/1: hexane/EtOAc→2/3: hexane/EtOAc) to give 3.8 mg of 117a.

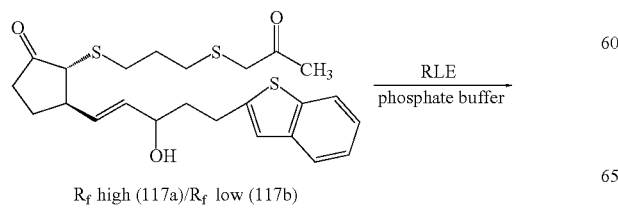

R$_f$ high (117a)/R$_f$ low (117b)

-continued

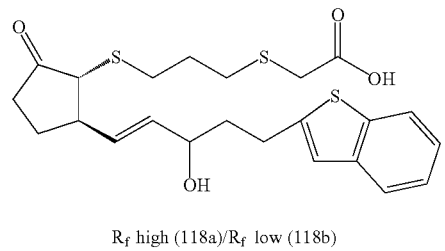

R$_f$ high (118a)/R$_f$ low (118b)

Rabbit liver esterase (3.0 mg, 300 μmole) was added to a solution of 117a (3.0 mg, 0.0062 mmole) in phosphate buffer/MeCN (1.5 ml/0.2 ml). After 16 hours at room temperature, the mixture was loaded on flash column chromatography (2/1: EtOAc/hexane→100% EtOAc) to give 1.6 mg of 118a.

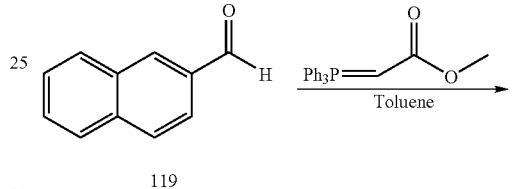

119

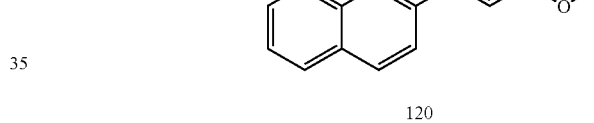

120

Methyl(triphenyl phosphoranylidene)acetate (8.5 g, 25.6 mmole) was added to a solution of 119 (2.1 g, 12.8 mmole) in toluene (200 ml). After 16 hours at room temperature, the mixture was concentrated in vacuo and the crude was loaded on a pack of silica gel in suction filter and washed with a solvent (8/1: hexane/EtOAc). The combined organics were concentrated in vacuo to give 2.7 g of 120.

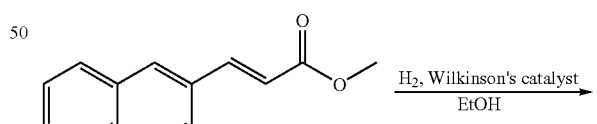

120

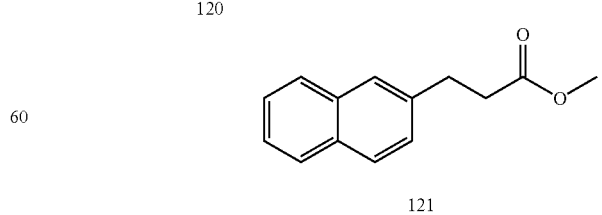

121

Chlorotris(triphenyl phosphine)rhodium (1.1 g, 1.2 mmole) was added to a solution of 120 (2.7 g, 0.012 mole)

in EtOH (100 ml). The mixture was charged with H$_2$ and stirred at room temperature for 3 days. The mixture was then concentrated in vacuo and purified by flash column chromatography (9/1: hexane/EtOAc) to give 2.7 g of 121.

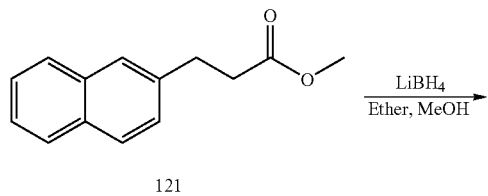

Lithium borohydride (0.77 g, 0.035 mole) was added to a solution of 121 (2.7 g, 0.012 mole) in ether (200 ml) at 0° C., followed by the addition of MeOH (1.1 g, 0.035 mole). The mixture was then warmed to room temperature and stirred for 2 hours. After TLC indicated no starting materials, the mixture was cooled to 0° C. and aqueous solution of NaOH was added dropwise. After 1 hour of stirring, the mixture was combined with brine and extracted with EtOAc (×3). The combined organics were washed with brine, dried (Na$_2$SO$_4$), concentrated in vacuo, and purified by flash column chromatography (100% DCM→1/1: DCM/EtOAc) to give 2.3 g of 122.

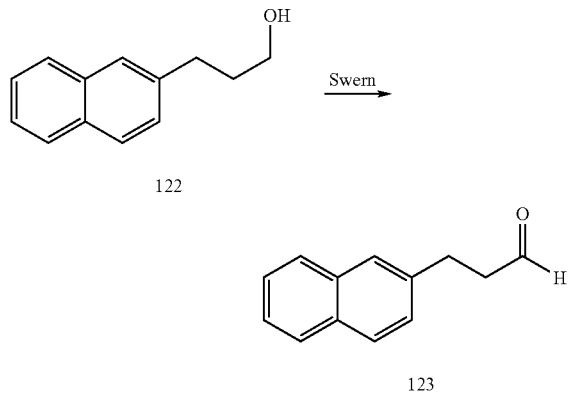

Dimethyl sulfoxide (3.5 ml, 49 mmole) was added dropwise to a solution of oxayl chloride (12 ml, 24 mmole) in DCM (150 ml) at −78° C. After 5 minutes, a solution of 122 (2.3 g, 12 mmole) in DCM (40 ml) was added and stirred for 1 hour at −78° C. After the addition of triethylamine (9.9 g, 98 mmole), the mixture was warmed to room temperature over 1 hour, poured into saturated NaHCO$_3$, and extracted with DCM (×3). The combined organics were washed with brine, dried (Na$_2$SO$_4$), concentrated in vacuo and purified by flash column chromatography (100% hexane→8/1: hexane/EtOAc) to give 2.1 g of 123.

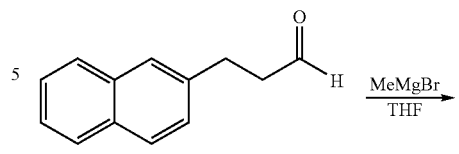

Methylmagunesium bromide (31.7 ml, 44.4 mmole) was added to a solution of 123 (2.1 g, 11 mmole) in THF (100 ml) at 0° C. The mixture was warmed to room temperature over 16 hours, quenched with saturated aqueous NH$_4$Cl and concentrated in vacuo. The crude was diluted with NH$_4$Cl and extracted with EtOAc (×3). The combined organics were washed with brine, dried (Na$_2$SO$_4$), concentrated in vacuo and purified by flash column chromatography (4/1: hexane/EtOAc) to give 1.9 g of 124.

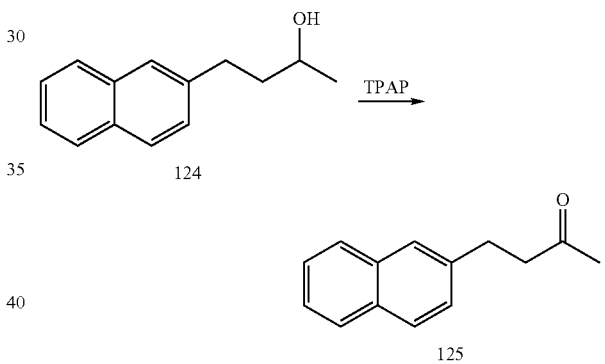

Tetrapropylammonium perruthenate (130 mg, 0.37 mmole) was added to a mixture of 124 (760 mg, 3.7 mmole), N-morpholine oxide (1.1 g, 9 mmole), and 4 Å° sieve (760 mg) in DCM (50 ml). After 1 hour, the mixture was purified by flash column chromatography (100% DCM) to give 710 mg of 125.

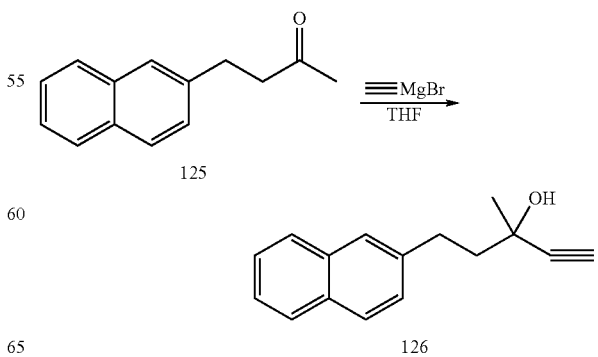

Ethynylmagunesium bromide (28 ml, 14 mmole) was added to a solution of 125 (710 mg, 3.5 mmole) in THF (50 ml) at 0° C. The mixture was warmed to room temperature over 16 hours, quenched with saturated aqueous NH₄Cl and concentrated in vacuo. The crude was diluted with NH₄Cl and extracted with EtOAc (×3). The combined organics were washed with brine, dried (Na₂SO₄), concentrated in vacuo and purified by flash column chromatography (1/1: DCM/Hexane) to give 720 mg of 126.

and purified by flash column chromatography (100% hexane→2/1: hexane/DCM) to give 1.0 g of 127.

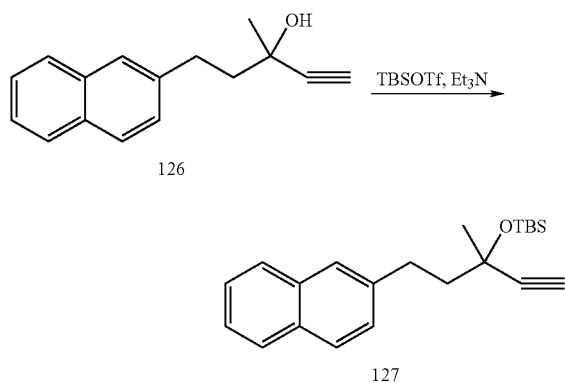

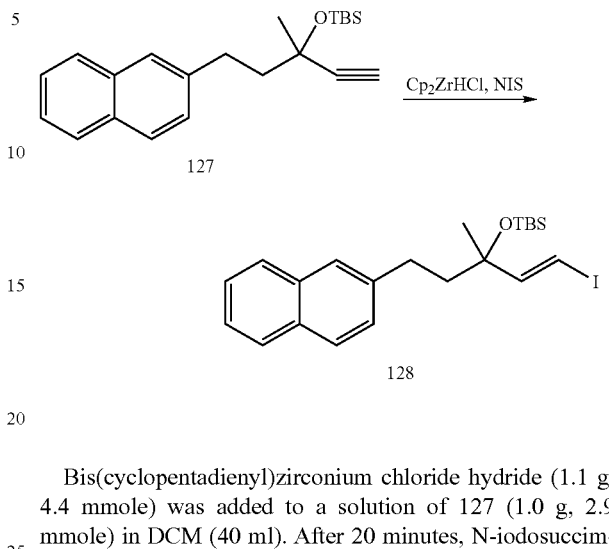

Tert-butyldimethyltrifluromethanesalformate (3.3 g, 12 mmole) was added to a mixture of 126 (720 mg, 3.1 mmole) and triethylamine (2.4 g, 24 mmole) in DCM (20 ml) at 0° C. After 1 hour at room temperature, NaHCO₃ was added and extracted with DCM (×3). The combined organics were washed with brine, dried (Na₂SO₄), concentrated in vacuo Bis(cyclopentadienyl)zirconium chloride hydride (1.1 g, 4.4 mmole) was added to a solution of 127 (1.0 g, 2.9 mmole) in DCM (40 ml). After 20 minutes, N-iodosuccimide (980 mg, 4.4 mole) was added and stirred for additional 1 hour. The mixture was then concentrated in vacuo (~5 ml of solvent) and loaded on flash column chromatography (100% hexane). The concentrated product was diluted with hexane, washed with sodium bisulfite (×2), brine, dried (Na₂SO₄), concentrated in vacuo, and purified by flash column chromatography (100% hexane) to give 1.1 g of 128.

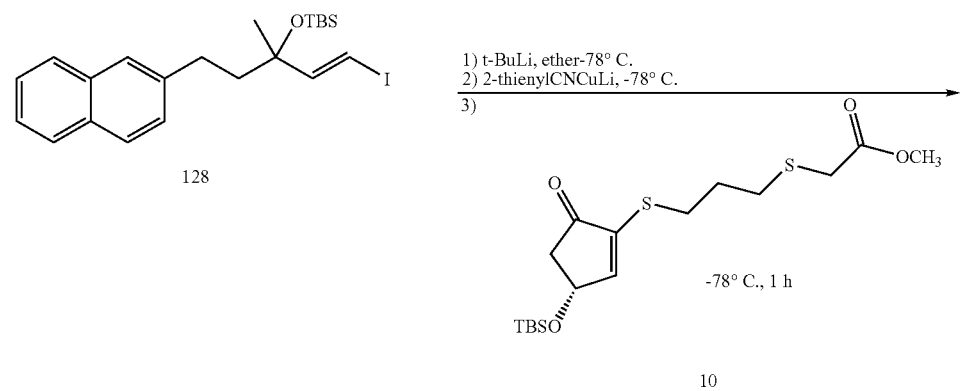

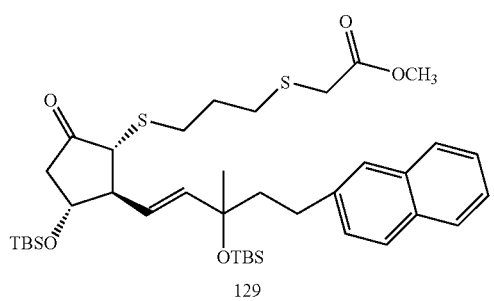

Tert-Butyl lithium (1.3 ml, 2.2 mmole) was added to a solution of 128 (510 mg, 1.1 mmole) in ether (2 ml) at −78° C. After 30 min, 2-thienylcyanocuprate lithium (1.3 mmole, 5.2 mmole) was added to the mixture and stirred for 30 minutes, at which point, a solution of 10 (310 mg, 0.78 mmole) in ether (1 ml) was added to the mixture. After stirring for one hour at −78° C., the mixture was quenched with saturated aqueous NH₄Cl and extracted with EtOAc (×3). The combined organics were washed with brine, dried (Na₂SO₄), concentrated in vacuo, and purified by flash column chromatography (9/1: hexane/EtOAc) to give 342 mg of 129.

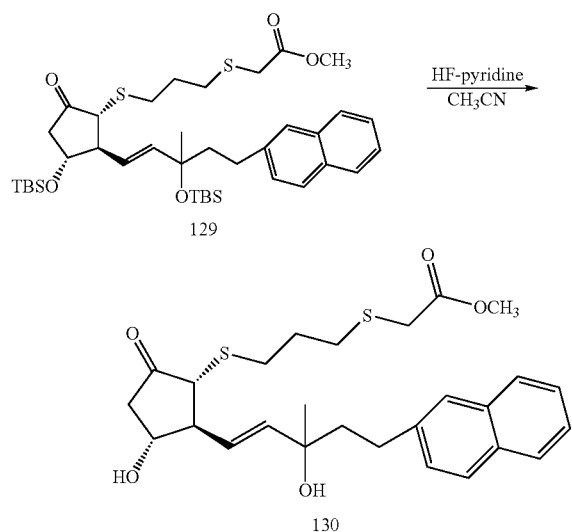

HF-pyridine (470 ul) was added to a solution of 129 (340 mg, 0.47 mmole) in MeCN (3 ml). After 2 hours at room temperature, the mixture was quenched with NaHCO₃ and extracted with EtOAc (×3). The combined organics were washed with saturated aqueous CuSO₄, brine, dried (Na₂SO₄), concentrated in vacuo, and purified by flash column chromatography (1/1: hexane/EtOAc) to give 90 mg of 130.

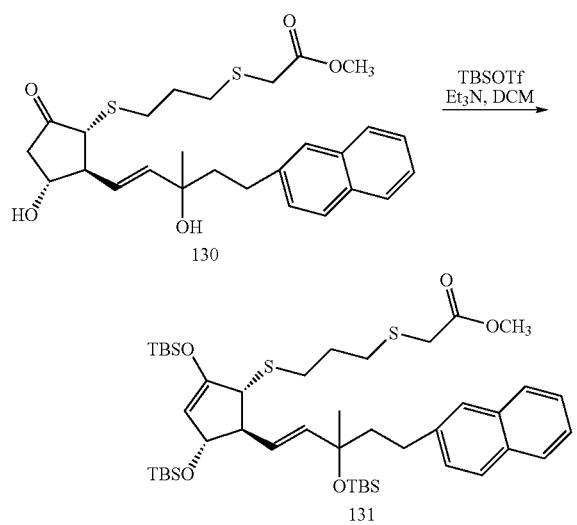

Tert-butyldimethyl trifluoromethanesulformate (190 mg, 0.72 mmole) was added to a mixture of 130 (90 mg, 0.18 mmole) and triethylamine (145 mg, 1.4 mmole) in DCM (5 ml) at 0° C. After 30 minutes stirring at room temperature, the mixture was quenched with NaHCO₃ and extracted with DCM (×3). The combined organics were washed with brine, dried (Na₂SO₄), concentrated in vacuo and purified by flash column chromatography (3% MeOH/DCM) to give 60 mg of 131.

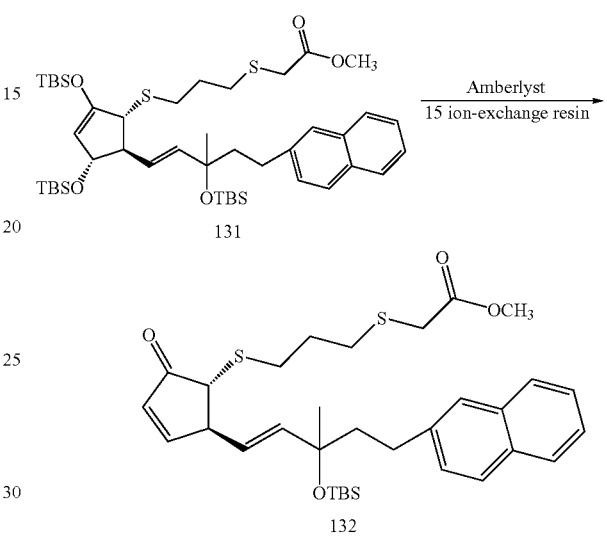

Amberlyst was added to a solution of 131 (60 mg, 0.071 mmole) in DCM (3 ml). After 3 hours stirring at room temperature, the mixture was loaded on flash column chromatography (9/1: hexane/EtOAc→4/1: hexane/EtOAc) to give 23 mg of 132.

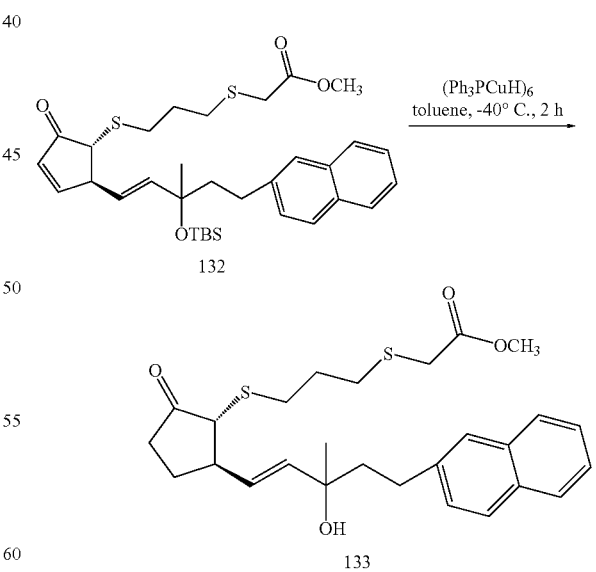

A solution of 132 (23 mg, 0.039 mmole) in toluene (2 ml) was added to a solution of Stryker's reagent (114 mg, 0.058 mmole) in toluene (10 ml) at −40° C. After stirring for 2 hours at −40° C., the mixture was quenched with NH₄OH/NH₄Cl (1/1) and stirred for 30 minutes until it became blue solution. The mixture was extracted with EtOAc (×1)+DCM (×2), and combined organics were washed with brine, dried (Na₂SO₄), concentrated in vacuo and purified by flash column chromatography (9/1: hexane/EtOAc→4/1: hexane/EtOAc) to give 14 mg of 133.

over 16 hours, quenched with saturated aqueous NH₄Cl and concentrated in vacuo. The crude was diluted with NH₄Cl and extracted with EtOAc (×3). The combined organics were washed with brine, dried (Na₂SO₄), concentrated in vacuo and purified by flash column chromatography (4/1: hexane/EtOAc) to give 2.67 g of 135.

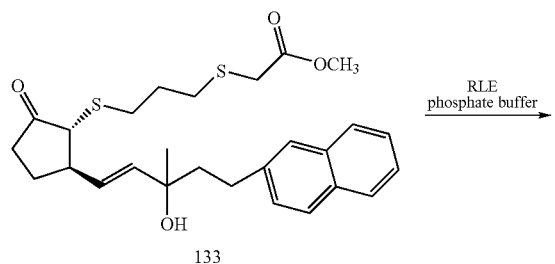

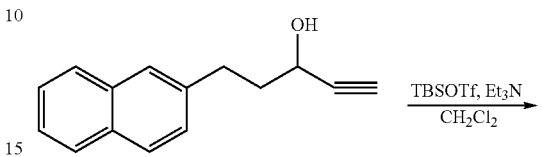

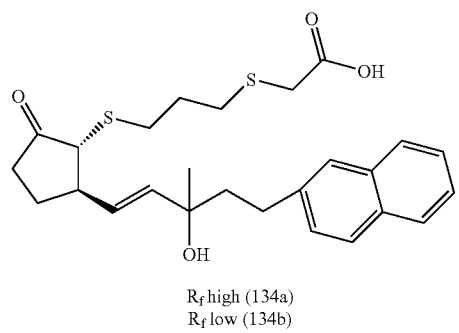

Tert-butyldimethyltrifluromethanesalfornate (3.1 g, 11.8 mmole) was added to a mixture of 135 (1.3 g, 5.9 mmole) and triethylamine (2.4 g, 23.6 mmole) in DCM (100 ml) at 0° C. After 1 hour at room temperature, NaHCO₃ was added and the solvent was removed in vacuo. Flash column chromatography (2/1: hexane/DCM) gave 1.87 g of 136.

Rabbit liver esterase (5.7 mg, 570 μmole) was added to a solution of 133 (5.7 mg, 0.012 mmole) in phosphate buffer/MeCN (2.7 ml/0.3 ml). After 16 hours at room temperature, the mixture was loaded on flash column chromatography (2/1: EtOAc/hexane→100% EtOAc) to give 1.0 mg of 134a and 2.5 mg of 134b

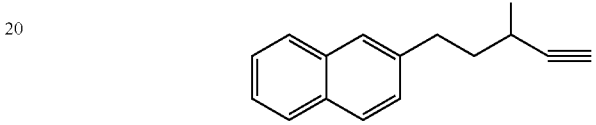

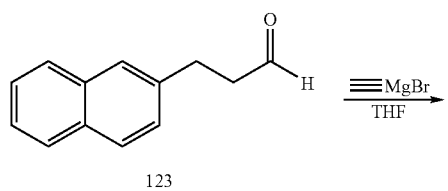

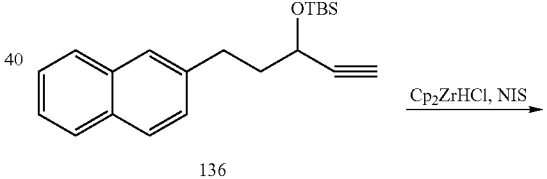

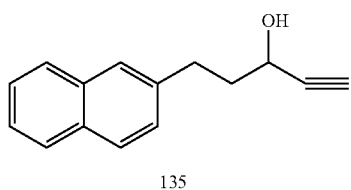

Ethynylmagunesium bromide (54.7 ml, 27.2 mmole) was added to a solution of 123 (3.3 g, 17.7 mmole) in THF (200 ml) at 0° C. The mixture was warmed to room temperature Bis(cyclopentadienyl)zirconium chloride hydride (2.2 g, 8.6 mmole) was added to a solution of 136 (1.9 g, 5.7 mmole) in DCM (100 ml). After 20 minutes, N-iodosuccimide (1.9 g, 8.6 mole) was added and stirred for additional 30 minutes. The mixture was then concentrated in vacuo (~10 ml of solvent) and loaded on flash column chromatography (100% hexane). The concentrated product was diluted with hexane, washed with sodium bisulfite (×2), brine, dried (Na₂SO₄), concentrated in vacuo, and purified by flash column chromatography (100% hexane→1% DCM/hexane) to give 1.7 g of 137.

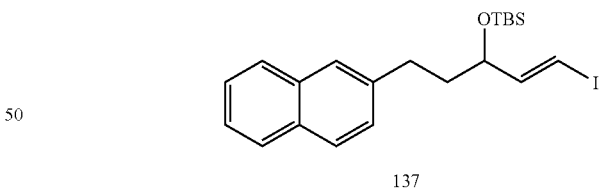

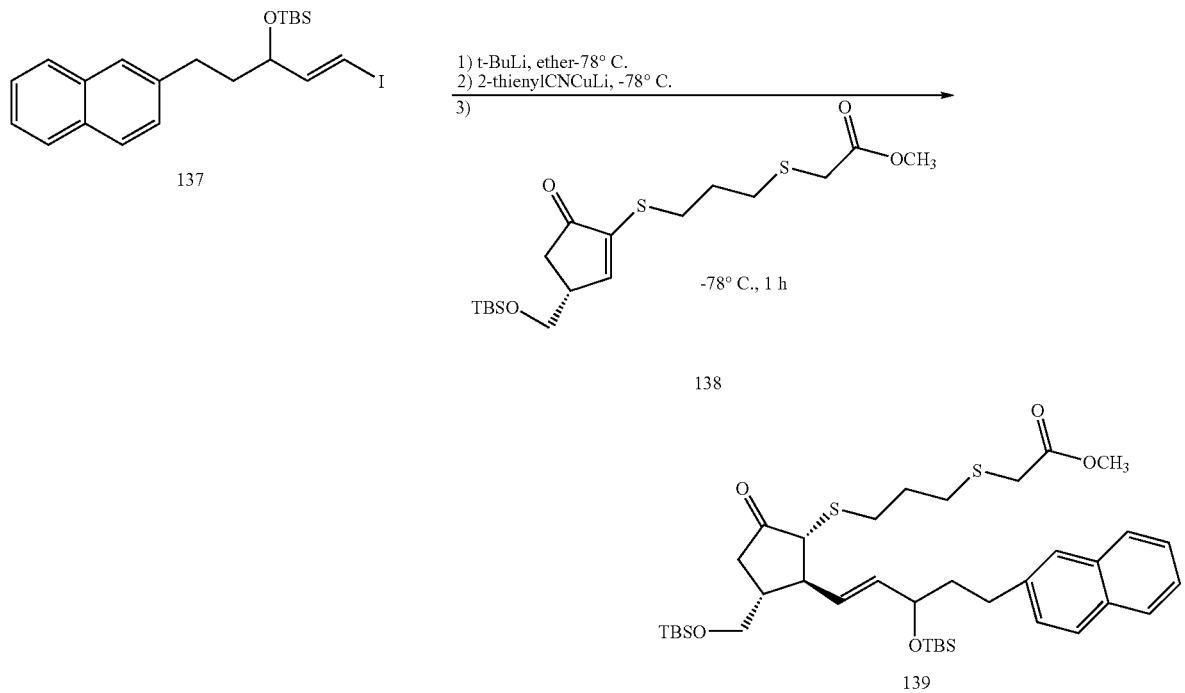

Tert-Butyl lithium (1.7 ml, 2.8 mmole) was added to a solution of 137 (595 mg, 1.4 mmole) in ether (2 ml) at −78° C. After 30 min, 2-thienylcyanocuprate lithium (6.7 ml, 1.7 mmole) was added to the mixture and stirred for 30 minutes, at which point, a solution of 138 (300 mg, 0.74 mmole) in ether (1 ml) was added to the mixture. After stirring for one hour at −78° C., the mixture was quenched with saturated aqueous $NH_4Cl$ and extracted with EtOAc (×3). The combined organics were washed with brine, dried ($Na_2SO_4$), concentrated in vacuo, and purified by flash column chromatography (9/1: hexane/EtOAc) to give 230 mg of 139.

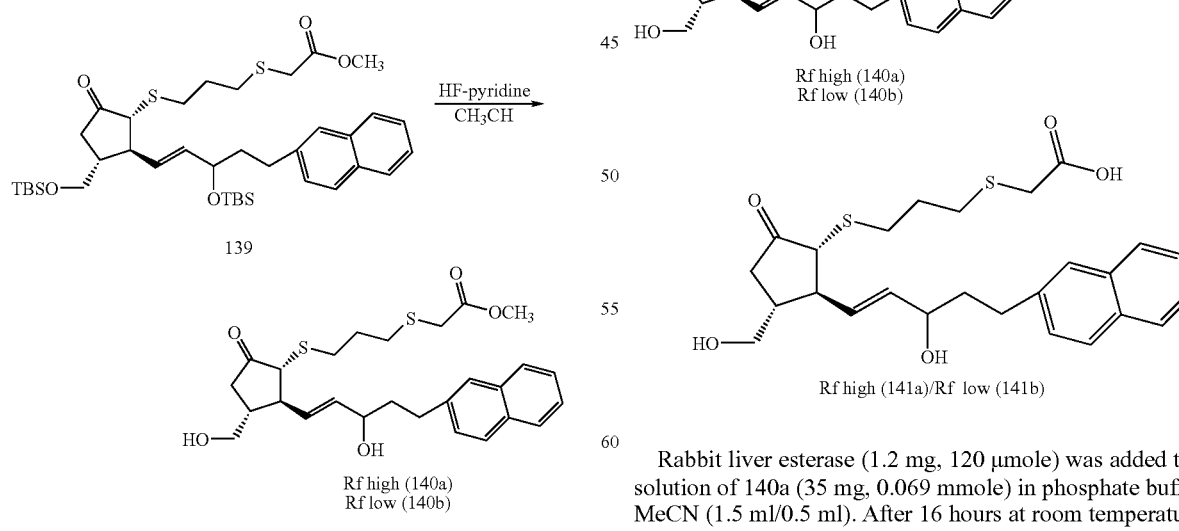

HF-pyridine (315 μl) was added to a solution of 139 (230 mg, 0.315 mmole) in MeCN (5 ml). After 2 hours at room temperature, the mixture was quenched with $NaHCO_3$ and extracted with EtOAc (×3). The combined organics were washed with brine, dried ($Na_2SO_4$), concentrated in vacuo, and purified flash column chromatography (3/1: EtOAc/Hexane→100% EtOAc) to give 57 mg of 140a and 50 mg of 140b.

Rabbit liver esterase (1.2 mg, 120 μmole) was added to a solution of 140a (35 mg, 0.069 mmole) in phosphate buffer/MeCN (1.5 ml/0.5 ml). After 16 hours at room temperature, the mixture was loaded on flash column chromatography (5% MeOH/EtOAc) to give 15 mg of 141a.

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

What is claimed is:

1. A compound comprising

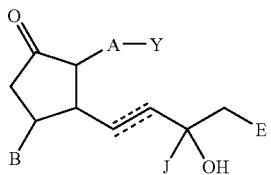

or a pharmaceutically acceptable salt or a prodrug thereof;
wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_qG(CH_2)_rG(CH_2)_s-$, wherein G is S or O, r is at least 2, and wherein q+r+s=4;

B is hydrogen, CN, $CO_2H$, $C_{1-6}$ hydrocarbyl, or $-(CH_2)_m X(CH_2)_pH$, wherein m is at least 1 and the sum of m and p is from 1 to 5;

X is S or O;

J is H, $CH_3$, or $CF_3$; and

E is a moiety comprising a covalently bonded chain of from 2 to 13 atoms.

2. The compound of claim 1 wherein B is H.
3. The compound of claim 1 wherein B is $CH_2OH$.
4. The compound of claim 1 wherein E is alkyl of 2 to 5 carbons.
5. The compound of claim 1 comprising

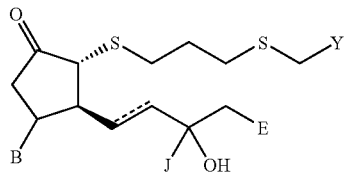

or a pharmaceutically acceptable salt or a prodrug thereof.

6. The compound of claim 4 wherein E is n-butyl.
7. The compound of claim 5 wherein E is R or $CH_2-R$, wherein R is an aromatic or heteroaromatic moiety having from 0 to 4 substituents having up to 6 non-hydrogen atoms each.
8. The compound of claim 7 wherein E is $CH_2-R$, wherein R is a bicyclic aromatic or heteroaromatic ring system which may have up to 2 substituents selected from the group consisting of methyl, ethyl, fluoro, bromo, chloro, trifluoromethyl, methoxy, and $NO_2$.
9. The compound of claim 8 wherein R is naphthyl or benzothienyl.
10. The compound of claim 5 wherein E is phenyl, benzyl, phenoxy, or phenylthio.
11. The compound of claim 2 wherein A is $-S(CH_2)_3SCH_2-$.
12. The compound of claim 5 comprising

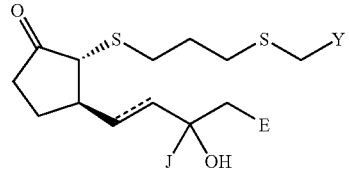

or a pharmaceutically acceptable salt or a prodrug thereof.

13. The compound of claim 12 wherein J is H.
14. The compound of claim 2 wherein J is H.
15. The compound of claim 1 wherein E is $R^1$ or $Z-R^1$, wherein $R^1$ is a bicyclic aromatic or heteroaromatic ring system having from 0 to 4 substituents having up to 6 non-hydrogen atoms, and wherein Z is O, S, or $CH_2$.
16. The compound of claim 15 wherein E is $Z-R^1$.
17. The compound of claim 16 wherein E is $CH_2-R^1$.
18. The compound of claim 1 wherein Y is selected from the group consisting of $CO_2(R^2)$, $CON(R^2)_2$, $CON(OR^2)R^2$, $CON(CH_2CH_2OH)_2$, $CONH(CH_2CH_2OH)$, $CH_2OH$, $P(O)(OH)_2$, $CONHSO_2R^2$, $SO_2N(R^2)_2$, $SO_2NHR^2$, and tetrazolyl-$R^2$; wherein $R^2$ is independently H, $C_1-C_6$ alkyl, phenyl, or biphenyl.
19. A compound of claim 18 which is selected from the group consisting of {3-[(1R,2R)-2-((E)-3-Hydroxy-3-methyl-5-naphthalen-2-yl-pent-1-enyl)-5-oxo-cyclopentylsulfanyl]-propyl-sulfanyl}-acetic acid;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid methyl ester;

{3-[(1R,2R)-2-((E)-5-Benzo[b]thiophen-2-yl-3-hydroxy-pent-1-enyl)-5-oxo-cyclopentylsulfanyl]-propylsulfanyl}-acetic acid methyl ester;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid methyl ester;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid methyl ester;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid;

{3-[(1R,2S,3R)-2-((E)-5-Benzo[b]thiophen-2-yl-3-hydroxy-pent-1-enyl)-3-hydroxymethyl-5-oxo-cyclopentylsulfanyl]-propylsulfanyl}-acetic acid;

{3-[(1R,2R)-2-((E)-3-Hydroxy-3-methyl-5-naphthalen-2-yl-pent-1-enyl)-5-oxo-cyclopentylsulfanyl]-propyl-sulfanyl}-acetic acid;

{3-[(1R,2R)-2-((E)-3-Hydroxy-5-naphthalen-2-yl-pent-1-enyl)-5-oxo-cyclopentylsulfanyl]-propylsulfanyl}-acetic acid methyl ester;

{3-[(1R,2R)-2-((E)-3-Hydroxy-5-naphthalen-2-yl-pent-1-enyl)-5-oxo-cyclopentylsulfanyl]-propylsulfanyl}-acetic acid methyl ester;
{3-[(1R,2R)-2-((E)-3-Hydroxy-5-naphthalen-2-yl-pent-1-enyl)-5-oxo-cyclopentylsulfanyl]-propylsulfanyl}-acetic acid;
{3-[(1R,2R)-2-((E)-3-Hydroxy-5-naphthalen-2-yl-pent-1-enyl)-5-oxo-cyclopentylsulfanyl]-propylsulfanyl}-acetic acid;
{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid methyl ester;
{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid methyl ester;
{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid;
{3-[(1R,2S,3R)-3-Hydroxymethyl-2-((E)-3-hydroxy-5-naphthalen-2-yl-pent-1-enyl)-5-oxo-cyclopentylsulfanyl]-propylsulfanyl}-acetic acid;
{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid methyl ester;
{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid methyl ester;
{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid;
{3-[(1R,2R)-2-((E)-3-Hydroxy-4-phenyl-but-1-enyl)-5-oxo-cyclopentylsulfanyl]-propylsulfanyl}-acetic acid methyl ester;
{3-[(1R,2R)-2-((E)-3-Hydroxy-4-phenyl-but-1-enyl)-5-oxo-cyclopentylsulfanyl]-propylsulfanyl}-acetic acid methyl ester;
{3-[(1R,2R)-2-((E)-3-Hydroxy-4-phenyl-but-1-enyl)-5-oxo-cyclopentylsulfanyl]-propylsulfanyl}-acetic acid;
{3-[(1R,2R)-2-((E)-3-Hydroxy-4-phenyl-but-1-enyl)-5-oxo-cyclopentylsulfanyl]-propylsulfanyl}-acetic acid;
{3-[(1R,2R)-2-((E)-3-Hydroxy-3-methyl-5-naphthalen-2-yl-pent-1-enyl)-5-oxo-cyclopentylsulfanyl]-propylsulfanyl}-acetic acid methyl ester;
{3-[(1R,2S,3R)-3-Hydroxymethyl-2-((E)-3-hydroxy-4-phenyl-but-1-enyl)-5-oxo-cyclopentylsulfanyl]-propylsulfanyl}-acetic acid;
{3-[3-Hydroxymethyl-2-(3-hydroxy-4-phenyl-but-1-enyl)-5-oxo-cyclopentylsulfanyl]-propylsulfanyl}-acetic acid isopropyl ester;
{3-[(1R,2R)-2-((E)-(S)-3-Hydroxy-oct-1-enyl)-5-oxo-cyclopentylsulfanyl]-propylsulfanyl}-acetic acid;
{3-[(1R,2R)-2-((E)-3-Hydroxy-4-naphthalen-2-yl-but-1-enyl)-5-oxo-cyclopentylsulfanyl]-propylsulfanyl}-acetic acid;
{3-[(1R,2R)-2-((E)-3-Hydroxy-4-naphthalen-2-yl-but-1-enyl)-5-oxo-cyclopentylsulfanyl]-propylsulfanyl}-acetic acid methyl ester;
{3-[2-(4-Benzo[b]thiophen-3-yl-3-hydroxy-but-1-enyl)-5-oxo-cyclopentylsulfanyl]-propylsulfanyl}-acetic acid;
{3-[2-(4-Benzo[b]thiophen-3-yl-3-hydroxy-but-1-enyl)-5-oxo-cyclopentylsulfanyl]-propylsulfanyl}-acetic acid; and
(3-{(1R,3R)-2-[(E)-5-(3-Chloro-benzo[b]thiophen-2-yl)-3-hydroxy-pent-1-enyl]-3-methyl-5-oxo-cyclopentylsulfanyl}-propylsulfanyl)-acetic acid methyl ester
or a pharmaceutically acceptable salt or a prodrug thereof.

20. A liquid comprising a compound, wherein said liquid is pharmaceutically acceptable, said compound comprising

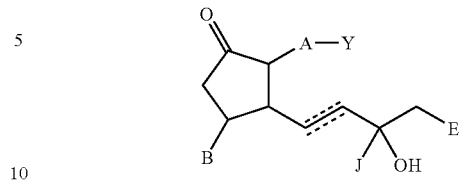

or a pharmaceutically acceptable salt or a prodrug thereof; wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_qG(CH_2)_rG(CH_2)_s-$, wherein G is S or O, r is at least 2, and wherein q+r+s=4;

B is hydrogen, CN, $CO_2H$, $C_{1-6}$ hydrocarbyl, or $-(CH_2)_mX(CH_2)_pH$, wherein m is at least 1 and the sum of m and p is from 1 to 5;

X is S or O;

J is H, $CH_3$, or $CF_3$; and

E is a moiety comprising a covalently bonded chain of from 2 to 13 atoms.

21. A method comprising administering a compound to a mammal for the treatment of glaucoma or ocular hypertension, said compound comprising

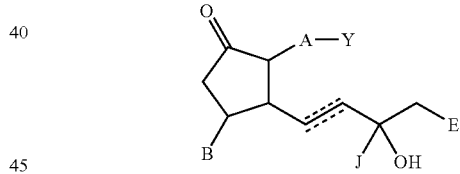

or a pharmaceutically acceptable salt or a prodrug thereof; wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_qG(CH_2)_rG(CH_2)_s-$, wherein G is S or O, r is at least 2, and wherein q+r+s=4;

B is hydrogen, CN, $CO_2H$, $C_{1-6}$ hydrocarbyl, or $-(CH_2)_mX(CH_2)_pH$, wherein m is at least 1 and the sum of m and p is from 1 to 5;

X is S or O;

J is H, $CH_3$, or $CF_3$; and

E is a moiety comprising a covalently bonded chain of from 2 to 13 atoms.

22. A pharmaceutical product, comprising a container adapted to dispense a compound in an ophthalmic liquid from said container in metered form; said compound comprising

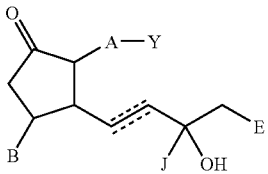

or a pharmaceutically acceptable salt or a prodrug thereof; wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_qG(CH_2)_rG(CH_2)_s-$, wherein G is S or O, r is at least 2, and wherein q+r+s=4;

B is hydrogen, CN, $CO_2H$, $C_{1-6}$ hydrocarbyl, or $-(CH_2)_m X(CH_2)_pH$, wherein m is at least 1 and the sum of m and p is from 1 to 5;

X is S or O;

J is H, $CH_3$, or $CF_3$; and

E is a moiety comprising a covalently bonded chain of from 2 to 13 atoms.

23. The compound of claim 1 wherein B is $CH_3$.

24. The compound of claim 1 wherein J is H.

25. The compound of claim 13 wherein E is naphthyl.

26. The compound of claim 25 comprising

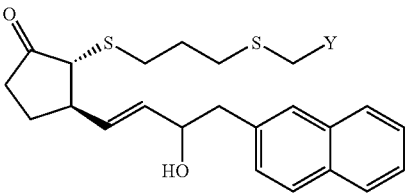

or a pharmaceutically acceptable salt or a prodrug thereof.

27. The compound of claim 7 wherein R is naphthyl or benzothienyl.

28. A method comprising administering a compound to a mammal suffering from an inflammatory bowel disease for the treatment of said disease, said compound comprising

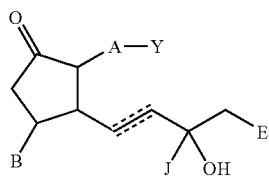

or a pharmaceutically acceptable salt or a prodrug thereof; wherein a dashed line represents the presence or absence of a bond;

Y is a carboxylic acid, sulfonic acid, or phosphonic acid functional group; or an amide or ester thereof comprising from 0 to 12 carbon atoms; or Y is hydroxymethyl or an ether thereof comprising from 0 to 12 carbon atoms; or Y is a tetrazolyl functional group;

A is $-(CH_2)_qG(CH_2)_rG(CH_2)_s-$, wherein G is S or O, r is at least 2, and wherein q+r+s=4;

B is hydrogen, CN, $CO_2H$, $C_{1-6}$ hydrocarbyl, or $-(CH_2)_m X(CH_2)_pH$, wherein m is at least 1 and the sum of m and p is from 1 to 5;

X is S or O;

J is H, $CH_3$, or $CF_3$; and

E is a moiety comprising a covalently bonded chain of from 2 to 13 atoms.

* * * * *

UNITED STATES PATENT AND TRADEMARK OFFICE
CERTIFICATE OF CORRECTION

PATENT NO. : 7,183,324 B2
APPLICATION NO. : 10/997039
DATED : February 27, 2007
INVENTOR(S) : Donde et al.

It is certified that error appears in the above-identified patent and that said Letters Patent is hereby corrected as shown below:

Column 2, line 67, delete "883-893)" and insert -- 883-893.) --, therefor.

Column 9, line 35, delete "unsubsituted" and insert -- unsubstituted --, therefor.

Column 18, line 15, delete "U46619" and insert -- U-46619 --, therefor.

Columns 25-26 (Table 1), line 6, delete "140" and insert -- 1400 --, therefor.

Column 33-34 (Table 1), line 6, delete "600" and insert -- 6000 --, therefor.

Column 33-34 (Table 1), line 6, delete ">10000  7244  3.7" and insert -- 7244  3.7 --, (under sub heading "HEP3A" and "HEP4" respectively).

Column 39, line 60 delete "-enyl]4-" and insert -- -enyl]-4- --, therefor.

Column 39, line 65, delete "ws" and insert -- was --, therefor.

Column 41, line 20, delete "(NaSO$_4$)," and insert -- (Na$_2$SO$_4$), --, therefor.

Column 44, line 12, delete "Tert-butyldimethyltrifluromethanesalformate" and insert -- Tert-butyldimethyltrifluromethanesulfonate --, therefor.

Column 45, line 22, delete "mole)" and insert -- mmole) --, therefor.

Column 45, line 54, delete "60 Å°," and insert -- 60 Å, --, therefor.

Column 46, line 32, delete "trifluoromethanesulformate" and insert -- trifluoromethanesulfonate --, therefor.

Column 47, line 52, delete "NAHCO$_3$" and insert -- NaHCO$_3$ --, therefor.

UNITED STATES PATENT AND TRADEMARK OFFICE
CERTIFICATE OF CORRECTION

PATENT NO.        : 7,183,324 B2
APPLICATION NO. : 10/997039
DATED             : February 27, 2007
INVENTOR(S)       : Donde et al.

It is certified that error appears in the above-identified patent and that said Letters Patent is hereby corrected as shown below:

Column 47, lines 59-64, delete " 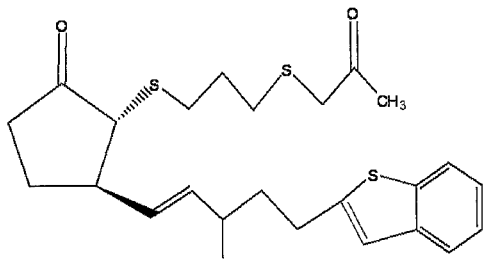 " and insert -- 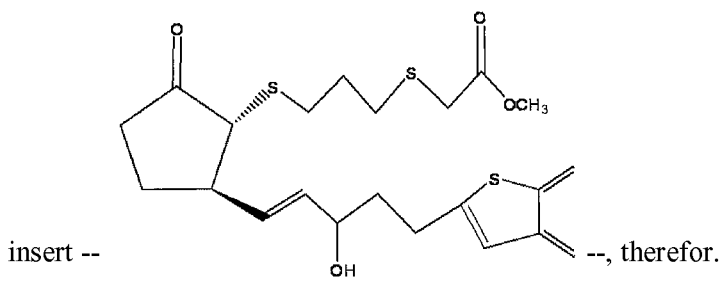 --, therefor.

Column 50, line 47, delete "4 Å°" and insert -- 4 Å --, therefor.

Column 51, line 28, delete "Tert-butyldimethyltrifluromethanesalformate" and insert -- Tert-butyldimethyltrifluromethanesulfonate --, therefor.

Column 54, line 1, delete "trifluoromethanesulformate" and insert -- trifluoromethanesulfonate --, therefor.

Column 55, line 43, after "134b" insert -- . --.

Column 57, line 48, delete "$CH_3CH$" and insert -- $CH_3CN$ --, therefor.

Signed and Sealed this

Sixteenth Day of October, 2007

JON W. DUDAS
*Director of the United States Patent and Trademark Office*

UNITED STATES PATENT AND TRADEMARK OFFICE
CERTIFICATE OF CORRECTION

PATENT NO. : 7,183,324 B2
APPLICATION NO. : 10/997039
DATED : February 27, 2007
INVENTOR(S) : Donde et al.

It is certified that error appears in the above-identified patent and that said Letters Patent is hereby corrected as shown below:

Column 2, line 67, delete "883-893)" and insert -- 883-893.) --, therefor.

Column 9, line 35, delete "unsubsituted" and insert -- unsubstituted --, therefor.

Column 18, line 15, delete "U46619" and insert -- U-46619 --, therefor.

Columns 25-26 (Table 1), line 6, delete "140" and insert -- 1400 --, therefor.

Column 33-34 (Table 1), line 6, delete "600" and insert -- 6000 --, therefor.

Column 33-34 (Table 1), line 6, delete ">10000  7244  3.7" and insert -- 7244  3.7 --, (under sub heading "HEP3A" and "HEP4" respectively).

Column 39, line 60, delete "-enyl]4-" and insert -- -enyl]-4- --, therefor.

Column 39, line 65, delete "ws" and insert -- was --, therefor.

Column 41, line 20, delete "($NaSO_4$)," and insert -- ($Na_2SO_4$), --, therefor.

Column 44, line 12, delete "Tert-butyldimethyltrifluromethanesalformate" and insert -- Tert-butyldimethyltrifluromethanesulfonate --, therefor.

Column 45, line 22, delete "mole)" and insert -- mmole) --, therefor.

Column 45, line 54, delete "60 Å°," and insert -- 60 Å --, therefor.

Column 46, line 32, delete "trifluoromethanesulformate" and insert -- trifluoromethanesulfonate --, therefor.

Column 50, line 47, delete "4 Å°" and insert -- 4 Å --, therefor.

Column 51, line 28, delete "Tert-butyldimethyltrifluromethanesalformate" and insert -- Tert-butyldimethyltrifluromethanesulfonate --, therefor.

Column 54, line 1, delete "trifluoromethanesulformate" and insert -- trifluoromethanesulfonate --, therefor.

Column 55, line 43, after "134b" insert -- . --.

UNITED STATES PATENT AND TRADEMARK OFFICE
CERTIFICATE OF CORRECTION

PATENT NO. : 7,183,324 B2
APPLICATION NO. : 10/997039
DATED : February 27, 2007
INVENTOR(S) : Donde et al.

It is certified that error appears in the above-identified patent and that said Letters Patent is hereby corrected as shown below:

Column 57, line 48, delete "$CH_3CH$" and insert -- $CH_3CN$ --, therefor.

Signed and Sealed this

Twenty-fifth Day of December, 2007

JON W. DUDAS
*Director of the United States Patent and Trademark Office*